(12) United States Patent
  Clough

(10) Patent No.: US 8,310,179 B2
(45) Date of Patent: Nov. 13, 2012

(54) PATIENT-LIFTING-DEVICE CONTROLS

(75) Inventor: Bradford A. Clough, Largo, FL (US)

(73) Assignee: Altorr Corp., Largo, FL (US)

( * ) Notice: Subject to any disclaimer, the term of this patent is extended or adjusted under 35 U.S.C. 154(b) by 455 days.

(21) Appl. No.: 12/698,133

(22) Filed: Feb. 1, 2010

(65) Prior Publication Data

US 2010/0192296 A1    Aug. 5, 2010

Related U.S. Application Data

(60) Provisional application No. 61/148,394, filed on Jan. 30, 2009, provisional application No. 61/164,955, filed on Mar. 31, 2009.

(51) Int. Cl.
  *H02P 1/00*    (2006.01)
(52) U.S. Cl. ........ 318/266; 318/264; 318/265; 318/255; 318/256
(58) Field of Classification Search .................. 318/266, 318/255–256, 264–265
  See application file for complete search history.

(56) References Cited

U.S. PATENT DOCUMENTS

| | | | | |
|---|---|---|---|---|
| 4,435,862 A * | 3/1984 | King et al. | ......................... | 5/611 |
| 6,000,077 A * | 12/1999 | Cyr | .................................. | 5/618 |
| 7,154,397 B2 * | 12/2006 | Zerhusen et al. | .......... | 340/573.1 |
| 7,235,942 B2 * | 6/2007 | Nagaoka et al. | .............. | 318/466 |
| 7,315,535 B2 * | 1/2008 | Schuman | ...................... | 370/349 |

* cited by examiner

*Primary Examiner* — Walter Benson
*Assistant Examiner* — David Luo
(74) *Attorney, Agent, or Firm* — Michael Smith, Esq.

(57) ABSTRACT

Systems, methods and apparatus are provided through which in some multisensory implementations, a patient-lifting-device is controlled by voice recognition using a background noise filter, keyboard text input, synaptic control and/or a tongue tactile input commands. In some implementations, the command is rejected or accepted in reference to an analysis of the command, the analysis including an analysis of the authority of operator, competency and/or the state of mind of the operator.

20 Claims, 13 Drawing Sheets

VOICE DATA RECEIVER

LIFT-DEVICE-CONTROLLER

PATENT-LIFTING-DEVICE CONTROLS

RELATED APPLICATION

This application claims the benefit of U.S. Provisional Application Ser. No. 61/148,394, filed 30 Jan. 2009 under 35 U.S.C. 119(e).

This application claims the benefit of U.S. Provisional Application Ser. No. 61/164,955, filed 31 Mar. 2009 under 35 U.S.C. 119(e).

FIELD

This disclosure relates generally to control of electrical devices, and more particularly to control of patient-lifting-devices in medical facilities.

BACKGROUND

People with physical difficulties rely on external means to provide motion. The external means vary from physical assistance of another person, to an animal to lift and transport a person with physical difficulties, to electrically and/or hydraulically actuated lifting devices that physically lift and transport the person with physical difficulties.

Conventional control of the electrically and/or hydraulically actuated patient-lifting-devices has included a handheld keypad controller that includes buttons for up, down, forward, backward and stop movement. The patient-lifting-device is also known as a patient hoist or a lift.

DETAILED DESCRIPTION

In the following detailed description, reference is made to the accompanying drawings that form a part hereof, and in which is shown by way of illustration specific implementations which may be practiced. These implementations are described in sufficient detail to enable those skilled in the art to practice the implementations, and it is to be understood that other implementations may be utilized and that logical, mechanical, electrical and other changes may be made without departing from the scope of the implementations. The following detailed description is, therefore, not to be taken in a limiting sense.

Apparatus, systems, and methods of varying scope are described herein. In addition to the aspects and advantages described in this summary, further aspects and advantages will become apparent by reference to the drawings and by reading the detailed description that follows.

The detailed description is divided into five sections. In the first section, a system level overview is described. In the second section, apparatus of implementations are described. In the third section, implementations of methods are described. In the fourth section, hardware and the operating environments in conjunction with which implementations may be practiced are described. Finally, in the fifth section, a conclusion of the detailed description is provided.

In one aspect, a method of controlling a patient-lifting-device includes receiving audio information from a microphone, filtering environment background noise from the audio information, extracting a command associated with the patient-lifting-device, and performing the command by a lift-device-controller of the patient-lifting-device.

In yet another aspect, a method of controlling a patient-lifting-device includes extracting from the audio information an indicator of the authority of the speaker of the audio information which further includes identifying the speaker of the audio information by comparing a speech pattern of the human speaker a database of known humans and determining an identity of the human speaker, yielding the authority of the identified human.

In another aspect, a method to update a database of authorities for a patient-lifting-device includes recording a speech sample of a human, the human selected from the group of humans comprising human healthcare providers, human non-professional employees of a healthcare facility, patients, and friends, relatives and coworkers of the patient; and associating the recording with an authority of control of the patient-lifting-device.

System Level Overview

A system level overview of the operation of an implementation is described in this section of the detailed description.

Figure 1:
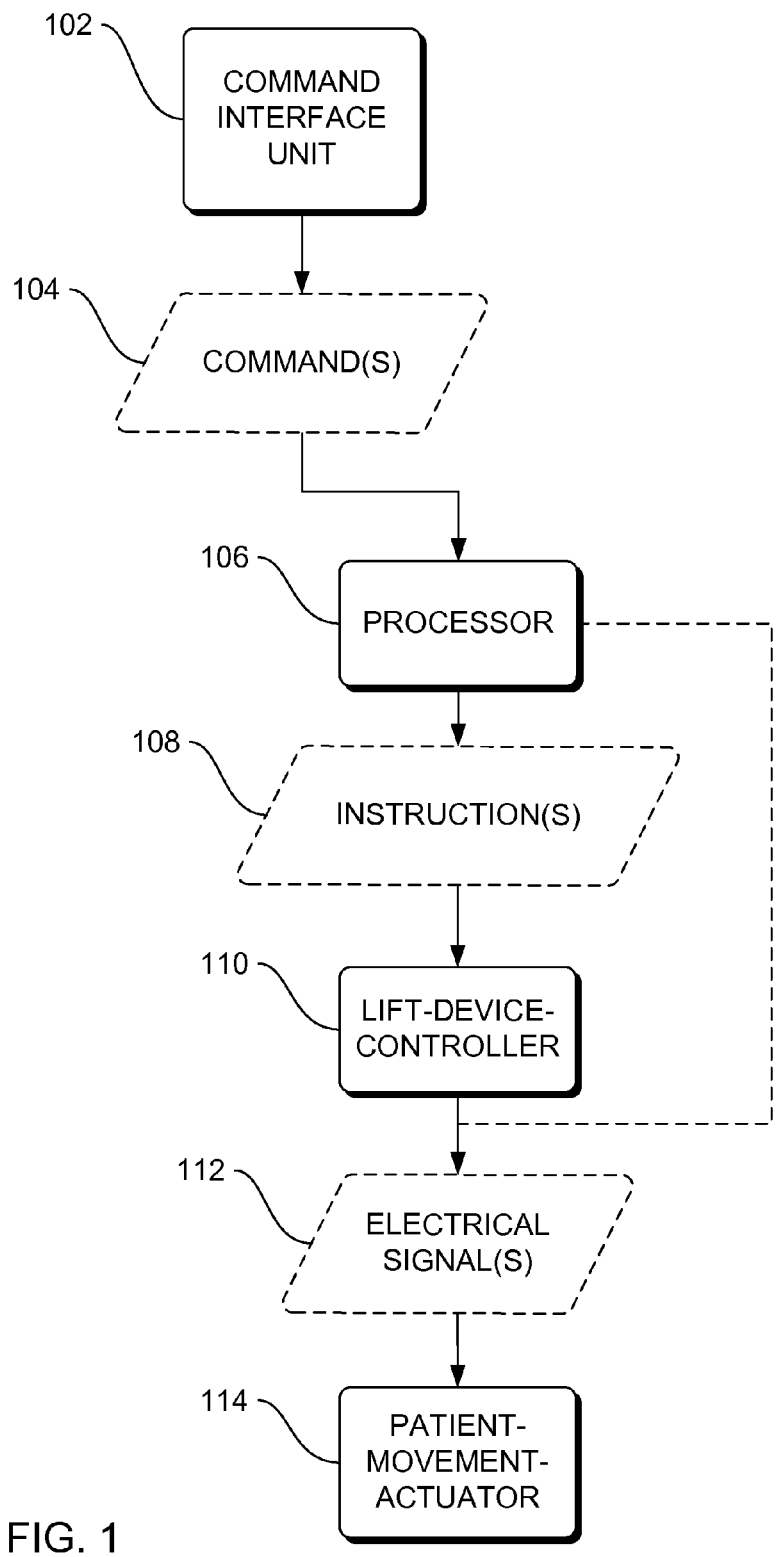
FIG. 1 is a block diagram of an overview of a system to control a patient-lifting-device, according to an implementation.

FIG. 1 is a block diagram of an overview of a system 100 to control a patient-lifting-device, according to an implementation. System 100 provides a convenient means to control an electrically-controlled patient-lifting-device.

System 100 includes a command interface unit 102 that receives information from a human in any one of a number of different communication methods and transmits command(s)

104 to a processor 106. Examples of commands 104 include "move up" "move down" "move forward" and "move backward." One implementation of the command interface unit 102 is described in FIG. 3 and another implementation of the command interface unit 102 is described in FIG. 4. In some implementations of the information that is received by the command interface unit 102, the information is multisensory audio input which is input from a number of sources, such as a keyboard, a hand-held keypad controller that includes buttons for up, down, forward, backward and stop, a synaptic activity sensor; and including audio input. The multisensory input is described in greater detail in FIG. 5.

In some implementations, the multisensory audio input includes only input from an audio source and input from a hand-held keypad controller.

The processor 106 in system 100 receives the command(s) 104 and generates one or more instruction(s) 108 that are specifically tailored for a lift-device-controller 110 that accomplishes the command.

The lift-device-controller 110 receives the instruction(s) 108 and generates one or more electric signal(s) 112 that are specifically tailored for a patient-movement-actuator 114 that accomplish or effectuate the one or more instruction(s) 108. The lift-device-controller 110 transmits the electrical signal(s) 112 to the patient-movement-actuator 114. One example of the patient-movement-actuator 114 is the patient-movement-actuator 1300 in FIG. 13. When the patient-lifting-device operates in accordance with the electrical signal(s) 112 from the lift-device-controller 110, the patient-movement-actuator 114 performs the command(s) 104 from the command interface unit 102.

In some implementations, the information that is received by the command interface unit 102 is audio information only. However, in some variations of these implementations, electrical control signals from a hand-held keypad controller are received by the patient-movement-actuator 114, along with electrical control signals 112 from the lift-device-controller 110 which provides dual, and only dual, multisensory control of the patient-movement-actuator 114 from the hand-held keypad controller and the audio information.

System 100 provides command control of the patient-movement-actuator 114 of a patient-lifting-device through a variety of input mediums, such verbal audio input, hand-held keypad controllers synaptic activity sensor. The multisensory command input benefits people with physical difficulties by reducing if not completely eliminating the requirement to manually control the patient-lifting-device.

Some implementations of system 100 do not include the instructions 108 and the lift-device-controller 110, and instead, the processor 106 is directly connected to the patient-movement-actuator 114 and the processor generates the electrical signals 112 that are specifically tailored for the patient-movement-actuator 114 that accomplish or effectuate the command(s) 104.

While the system 100 is not limited to any particular command interface unit 102, command(s) 104, processor 106, instruction(s) 108, lift-device-controller 110, electric signal(s) 112, and patient-movement-actuator 114, for sake of clarity a simplified command interface unit 102, command(s) 104, processor 106, instruction(s) 108, lift-device-controller 110, electric signal(s) 112, and patient-movement-actuator 114 are described.

Apparatus Implementations

In the previous section, a system level overview of the operation of an implementation was described. In this section, the particular apparatus of such an implementation are described by reference to a series of diagrams.

Figure 2:
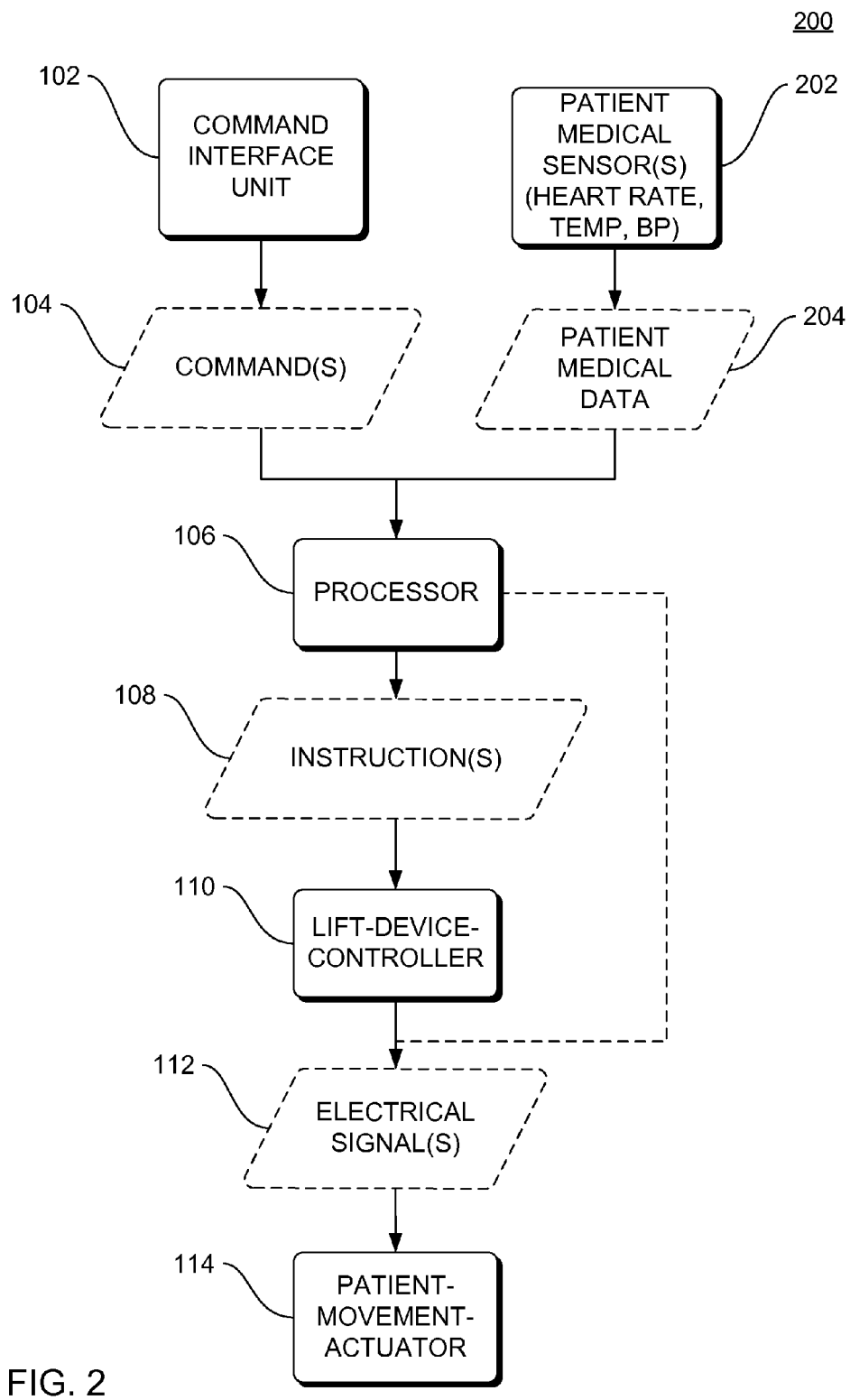
FIG. 2 is a block diagram of apparatus to control a patient-lifting-device in reference to patient medical condition, according to an implementation.

FIG. 2 is a block diagram of apparatus 200 to control a patient-lifting-device in reference to a patient medical condition, according to an implementation. Apparatus 200 provides a convenient means to control and electrically-controlled patient-lifting-device in reference to patient medical condition.

Apparatus 200 includes one or more sensor(s) 202 of patient condition. Examples of the sensor(s) 202 include heart rate sensor temperature sensor and blood pressure sensor. In apparatus 200, patient sensor data 204 from the patient medical sensor(s) 202 are received by the processor 106. The instruction(s) 108 that are generated by the processor from the command(s) 104 of the command interface unit 102 are generated in reference to the patient medical data 204. Thus apparatus 200 generates instruction(s) 108 that ultimately control the patient-lifting-device in any manner that is less detrimental to the patient in consideration of the medical condition of the patient as indicated by the patient medical sensor data 204.

Some implementations of apparatus 200 do not include the instructions 108 and the lift-device-controller 110, and instead, the processor 106 is directly connected to the patient-movement-actuator 114 and the processor generates the electrical signals 112 that are specifically tailored for the patient-movement-actuator 114 that accomplish or effectuate the command(s) 104.

Apparatus 200 provides command control of a patient-movement-actuator 114 of a patient-lifting-device through a variety of input mediums, such verbal audio input, hand-held keypad controllers synaptic activity sensor in reference or consideration to the medical condition of a patient. The multisensory command input benefits people with physical difficulties by reducing if not completely eliminating the requirement to manually control the patient-lifting-device.

Figure 3:
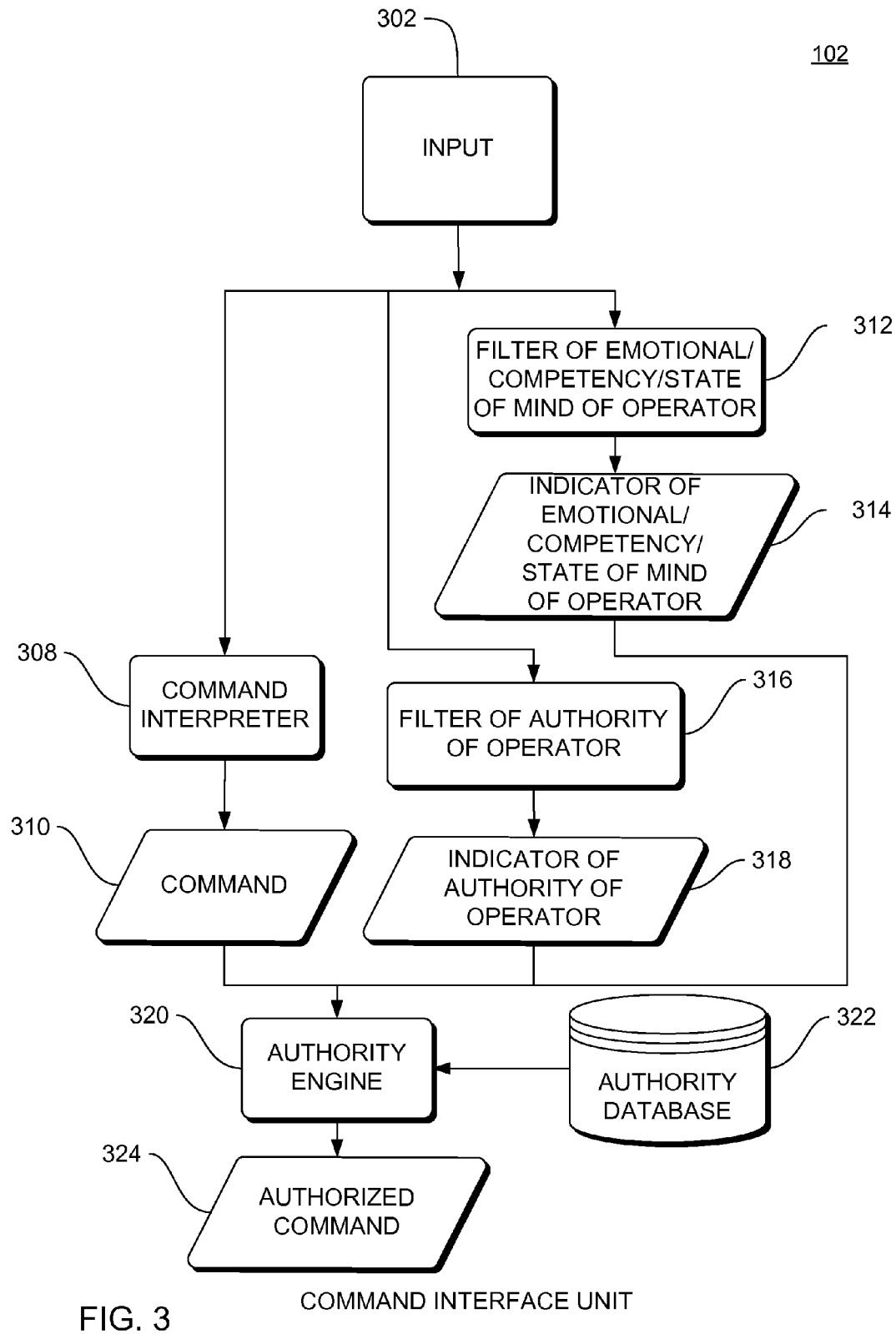
FIG. 3 is a block diagram of a command interface unit apparatus that according to an implementation receives information from a human and generates command(s) from the human information, in reference to authority of the human and the state of the mind of the human.

FIG. 3 is a block diagram of a command interface unit apparatus 300 that according to an implementation receives information from a human and generates command(s) 104 from the human information, in reference to authority of the human and the state of the mind of the human. Apparatus 300 provides command(s) 104 that are suitable to be processed by a processor in control of a patient-lifting-device that are generated in reference to the authority in the state of mind of the human. Apparatus 300 is one implementation of the command interface unit 102 and FIG. 1 and FIG. 2.

The command interface unit 102 shown in FIG. 3 includes an input device 302 that receives information in any one of a number of different communication methods. One implementation of a number of different input devices 302 is described in FIG. 5. Input that is captured as analog data or analog signals is converted to digital data by a conventional analog to digital converter (A/D).

The received information is processed in a three-pronged approach. In a first prong, the information is processed by a command interpreter 308. The command interpreter analyzes the information and extracts a command 310 from the information. Examples of commands 310 include "move up" "move down" "move forward" and "move backward." In a second prong, the information is processed by a state-of-mind filter 312. The state-of-mind filter 312 analyzes the information and extracts from the information indicators of the emotional state of the operator, indicators of the competency of the operator, and/or indicators of the state-of-mind of the operator 314. In a third prong, the information is processed by an authority filter 316. The authority FIG. 316 analyzes the information and extracts from the information an indicator 318 of the authority of the operator.

An authority engine 312 receives the command 310, the state-of-mind 314 and the indicator of authority of the operator 318. The authority engine 320 analyzes the command 310, the state-of-mind 314 and the indicator of authority of the operator 318 in reference to an authority database 322. In one implementation the authority engine determines whether or not the command 310 is authorized by the authority of the operator 318. If the command 310 is not authorized by the authority of the operator 318, the command 310 is rejected. In another implementation the authority engine 320 determines whether or not the state-of-mind 314 of the operator is of a sufficient level for the command 310. If the state-of-mind 314 for the operator is not of a sufficient level for the command 310, command 310 is rejected.

If the authority engine 320 determines that both the state-of-mind 314 and the authority 318 of the operator are sufficient for the command 310, the authority engine generates or designates an authorized command 324 from the command 310.

Command interface unit apparatus 300 provides command control of a patient-movement-actuator 114 of a patient-lifting-device through a variety of input mediums, such verbal audio input, hand-held keypad controllers synaptic activity sensor in reference or consideration to the authority and emotion, competency and state of mind of the operator from which the command is issued. The multisensory command input of command interface unit apparatus 300 benefits people with physical difficulties by reducing if not completely eliminating the requirement to manually control the patient-movement-actuator 114.

Figure 4:
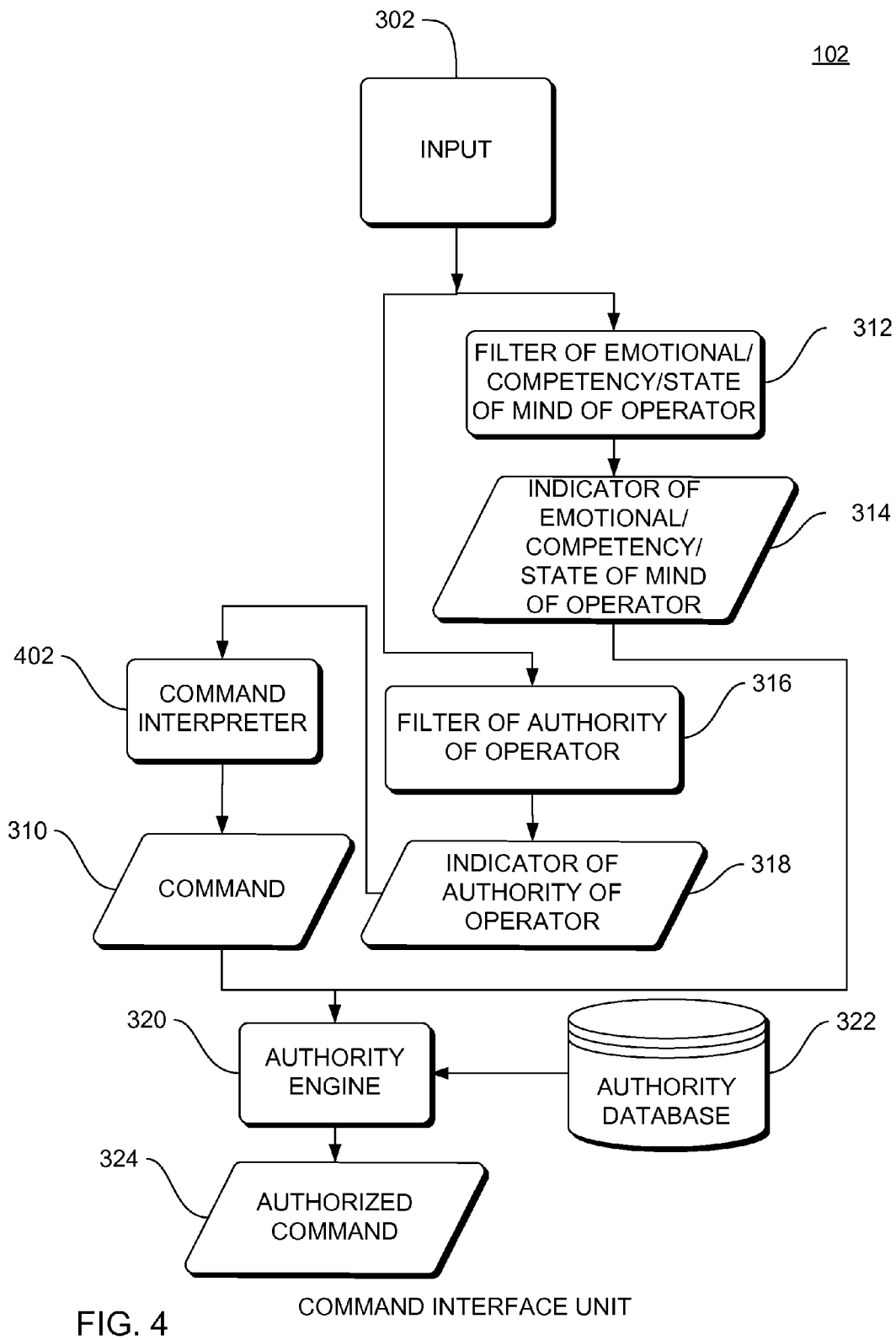
FIG. 4 is a block diagram of a command interface unit apparatus that according to an implementation receives information from a human and generates command(s) from the human information, in reference to authority of the human and the state of the mind of the human.

FIG. 4 is a block diagram of a command interface unit apparatus 400 that according to an implementation receives information from a human and generates command(s) 104 from the human information, in reference to authority of the human and the state of the mind of the human. Apparatus 400 provides command(s) 104 that are suitable to be processed by a processor in control of a patient-lifting-device that are generated in reference to the authority in the state of mind of the human. Apparatus 400 is one implementation of the command interface unit 102 and FIG. 1 and FIG. 2.

The command interface unit 102 shown in FIG. 4 includes an input device 402 that receives information in any one of a number of different communication methods. One implementation of a number of different input devices 402 is described in FIG. 5. The received information is processed in a two-pronged approach. In a first prong, the information is processed by an authority filter 316. The authority FIG. 316 analyzes the information and extracts from the information an indicator 318 of the authority of the operator. Thereafter, the information is processed by a command interpreter 402. The command interpreter analyzes the information and extracts a command 310 from the information. Examples of commands 310 include "move up" "move down" "move forward" and "move backward." In a second prong, the information is processed by a state-of-mind filter 312. The state-of-mind filter 312 analyzes the information and extracts from the information indicators of the emotional state of the operator, indicators of the competency of the operator, and/or indicators of the state-of-mind of the operator 314.

An authority engine 312 receives the command 310, the state-of-mind 314 and the indicator of authority of the operator 318. The authority engine 320 and analyzes the command 310, the state-of-mind 314 and the indicator of authority of the operator 318 in reference to an authority database 322. In one implementation the authority engine determines whether or not the command 310 is authorized by the authority of the operator 318. If the command 310 is not authorized by the authority of the operator 318, the command 310 is rejected. In another implementation the authority engine 320 determines whether or not the state-of-mind 314 of the operator is of a sufficient level for the command 310. If the authority for the operator is not of a sufficient level for the command 310, command 310 is rejected. If the authority for the operator is of a sufficient level for the command 310, command 310 is accepted.

Command interface unit apparatus 400 provides command control of a patient-movement-actuator 114 of a patient-lifting-device through a variety of input mediums, such verbal audio input, hand-held keypad controllers synaptic activity sensor in reference or consideration to the authority and emotion, competency and state of mind of the operator from which the command is issued, with the added efficiency of not interpreting the command from the input information until after the authority and emotion, competency and state of mind of the operator, as represented in the input information, is evaluated. The multisensory command input of command interface unit apparatus 400 benefits people with physical difficulties by reducing if not completely eliminating the requirement to manually control the patient-movement-actuator 114.

Figure 5:
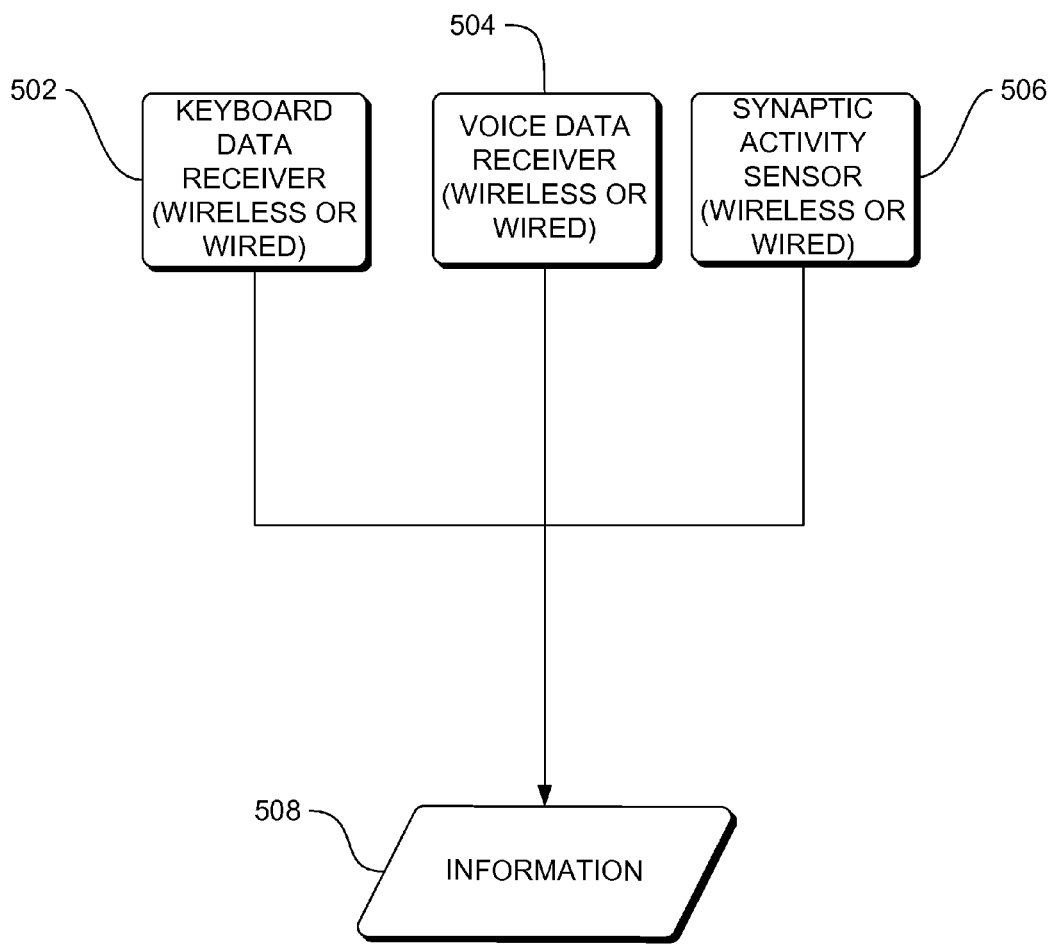
FIG. 5 is a block diagram of a plurality of input devices that receive information in any one of a number of different communication methods, according to an implementation.

FIG. 5 is a block diagram of a plurality of input devices 500 that receive information in any one of a number of different communication methods, according to an implementation. Input devices 500 are implementations of the input devices 302 and FIG. 3 and FIG. 4.

Input devices 302 include a conventional keyboard data receiver 502, commonly known as a keyboard. Input devices 302 also include an audio data receiver 504. Input devices also include a synaptic activity sensor 506. The receivers 502 and 504 and the synaptic activity sensor 506 can be implemented either with a wireless connection to the command interface unit 102 and/or with a wired connection to the command interface unit 102. Another input device that is not shown is a hand-held keypad controller that includes buttons for up, down, forward, backward and stop. The receivers 502 and 504, the hand-held keypad controller, and the synaptic activity sensor 506 capture multisensory information 508 from an operator that is processed by the command interface unit 102 in FIG. 1, FIG. 2 and/or FIG. 3. The multiple input devices of in FIG. 5 provide multisensory input to the command interface unit 102 in FIG. 1, FIG. 2 and/or FIG. 3.

A receiver that is not shown in FIG. 5 is a pressure sensitive device (e.g. piezo electric device) mounted on and/or in the top of a tooth. The pressure sensitive device senses/reads/measures pressure, transmits an indication or representation of the pressure to a processor via a wireless connection. The pressure reading/measurement is interpreted as an indicator or command to an external device, such as a patient-lifting-device. An example of the command is a command to control horizontal speed of the patient-lifting-device.

Input device 302 in FIG. 5 provides command control of a patient-movement-actuator 114 of a patient-lifting-device through a variety of input mediums, such verbal audio input, hand-held keypad controllers synaptic activity sensor in reference or consideration to the authority and emotion, competency and state of mind of the operator from which the command is issued. The multisensory command input of input device 302 in FIG. 5 benefits people with physical difficulties by reducing if not completely eliminating the requirement to manually control the patient-movement-actuator 114.

Figure 6:
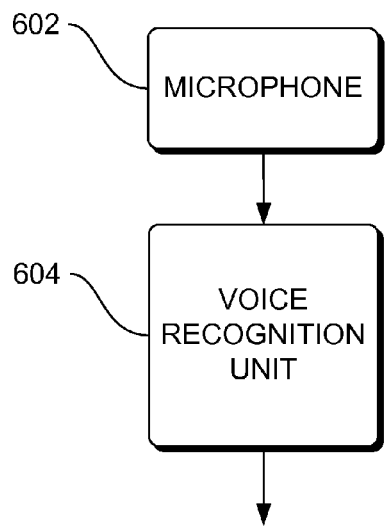
FIG. 6 is a block diagram of a voice data receiver that receives audio information, according to an implementation.

FIG. 6 is a block diagram of a voice data receiver 600 that receives audio information, according to an implementation.

Audio data receiver 504 in FIG. 6 is one implementation of the voice data receiver 504 in FIG. 5. The voice data receiver 504 in FIG. 6 includes a microphone 602 that is operably coupled to a voice recognition unit 604. In some implementations, the voice recognition unit 604 includes a component (not shown) that suppresses or filters background environmental noise.

Audio data receiver 504 in FIG. 6 provides command control of a patient-movement-actuator 114 through verbal audio input. The command audio input of audio data receiver 504 in FIG. 6 benefits people with physical difficulties by reducing if not completely eliminating the requirement to manually control the patient-movement-actuator 114.

Figure 7:
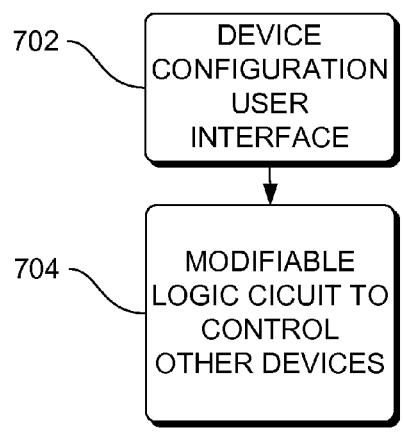
FIG. 7 is a block diagram of a lift-device-controller that receives instructions and generates electrical signals that control a patient-movement-actuator, according to an implementation.

FIG. 7 is a block diagram of a lift-device-controller 700 that receives instructions and generates electrical signals that control a patient-lifting-device, according to an implementation. Lift-device-controller 700 is one example of lift-device-controller 110 in FIG. 1, FIG. 2 and FIG. 11. The lift-device-controller 700 includes a user interface 702 for device configuration that is operable to display, receive and/or store device configuration information for a patient-movement-actuator, such as patient-movement-actuator 114 in FIG. 1 and FIG. 2. The device configuration user interface 702 is operably coupled to a modifiable logic circuit 704 that is operable to control the patient-lifting-device. In one implementation, the modifiable logic circuit 704 is a field-programmable gate-array (FPGA) circuit in reference to the device configuration.

Apparatus components of FIG. 1-7 can be embodied as computer hardware circuitry or as a computer-readable program, or a combination of both.

More specifically, in the computer-readable program implementation, the programs can be structured in an object-orientation using an object-oriented language such as Java, Smalltalk or C++, and the programs can be structured in a procedural-orientation using a procedural language such as COBOL or C. The software components communicate in any of a number of means that are well-known to those skilled in the art, such as application program interfaces (API) or interprocess communication techniques such as remote procedure call (RPC), common object request broker architecture (CORBA), Component Object Model (COM), Distributed Component Object Model (DCOM), Distributed System Object Model (DSOM) and Remote Method Invocation (RMI). In some implementations, the components execute on as few as one computer as in computer environment 1000 in FIG. 10, or on at least as many computers as there are components. In some implementations, the components execute on as few as one voice-recognition apparatus as in voice-recognition apparatus 1100 in FIG. 11, or on at least as many computers as there are components.

Method Implementations

In the previous section, apparatus of the operation of an implementation was described. In this section, the particular methods performed by a processor of such an implementation are described by reference to a series of flowcharts.

Figure 8:
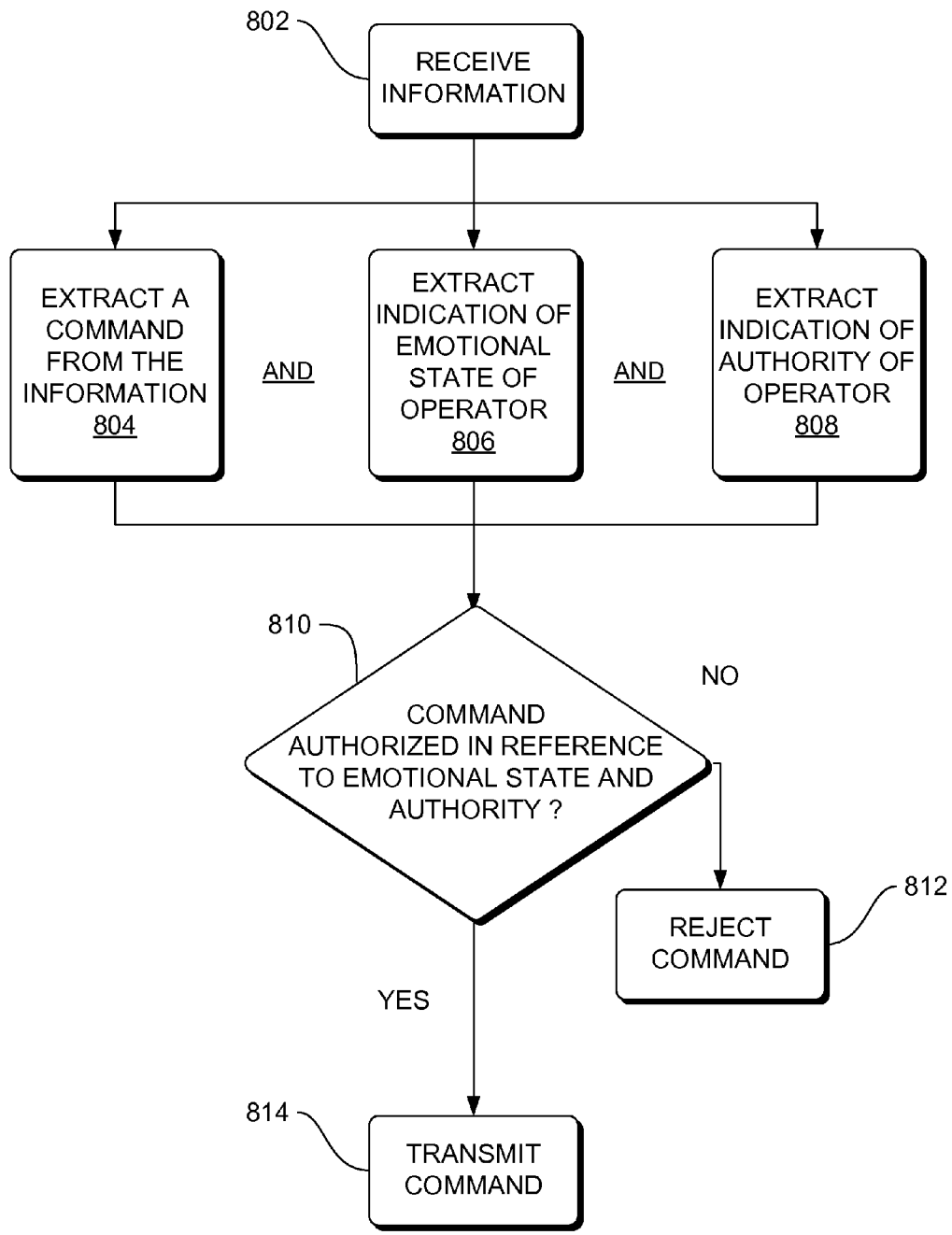
FIG. 8 is a flowchart of a method to control a patient-lifting-device, according to an implementation.

FIG. 8 is a flowchart of a method 800 to control a patient-lifting-device, according to an implementation. Method 800 receives information from a human and generates a command from the human information, in reference to authority of the human and the state of the mind of the human. Method 800 generates command(s) that are suitable to be processed by a processor in control of a patient-lifting-device. In some implementations, method 800 is performed by the command interface unit 102 and FIG. 1 and FIG. 2.

Method 800 includes receiving 802 information from any one of a number of different communication devices. FIG. 5 describes some implementations of communication devices. Method 800 includes processing the information by analyzing the information and extracting 804 a command from the information. Examples of the command include "move up" "move down" "move forward" and "move backward." Method 800 includes processing the information by analyzing and extracting 806 from the information indicators of the emotional state of the operator, indicators of the competency of the operator, and/or indicators of the state-of-mind of the operator.

Method 800 includes processing the information by analyzing the information and extracting 808 from the information an indicator of the authority of the operator. In some implementations, extracting an indication of authority of the operator includes identifying the operator. For example, where the information 802 is audio information from a human speaker, the identity of the human speaker is determined and the authority of that speaker is then determined. In some implementations, the speech pattern of the human speaker is compared to a database of known humans. The database is created prior to the performance of method 800 from recorded speech sample recordings of humans who are authorized to enter the healthcare facility, such a healthcare providers, non-professional employees of the healthcare facility, patients, and friends, relatives and/or coworkers of the patient. Each human whose speech sample is recorded in the database is associated with a particular authority. An example of an authority is "full authority" in which the human is authorized to exercise or command all functions of the patient-lifting-device. Another example of an authority is "no authority in which the human is not authorized to exercise or command any function of the patient-lifting-device. In method 800, the database is accessed and a comparison of the information 802 to the speech samples in the database is performed. When the comparing determines the identity of the human speaker, the authority of the identified human is accessed and used as the indicator of authority of the operator.

In method 800, the command, the state-of-mind and the indicator of authority of the operator is analyzed 810 to an authority database to determine whether or not the command is authorized by the authority of the operator in consideration of the emotional state of the operator. If the command is not authorized by the authority and emotional state of the operator, the command is rejected 812. In some implementations, rejecting 812 the command can include transmitting a notice of an attempted unauthorized command to supervisory personnel or law enforcement agency. If the command is determined to be authorized, the command is transmitted 814 to the processor (e.g. 106 in FIG. 1) and the command 812 is performed by the patient-lifting-device. In some implementations, a log or journal of all extracted commands in action 804 and the determination 810 of the authority of the extracted commands is stored.

Method 800 provides command control of a patient-movement-actuator 114 through a variety of input mediums, such verbal audio input, hand-held keypad controllers synaptic activity sensor in reference or consideration to the authority and emotion, competency and state of mind of the operator from which the command is issued, with the added efficiency of not interpreting the command from the input information until after the authority and emotion, competency and state of mind of the operator, as represented in the input information, is evaluated. The multisensory command input of method 800 benefits people with physical difficulties by reducing if not completely eliminating the requirement to manually control the patient-movement-actuator 114.

Figure 9:
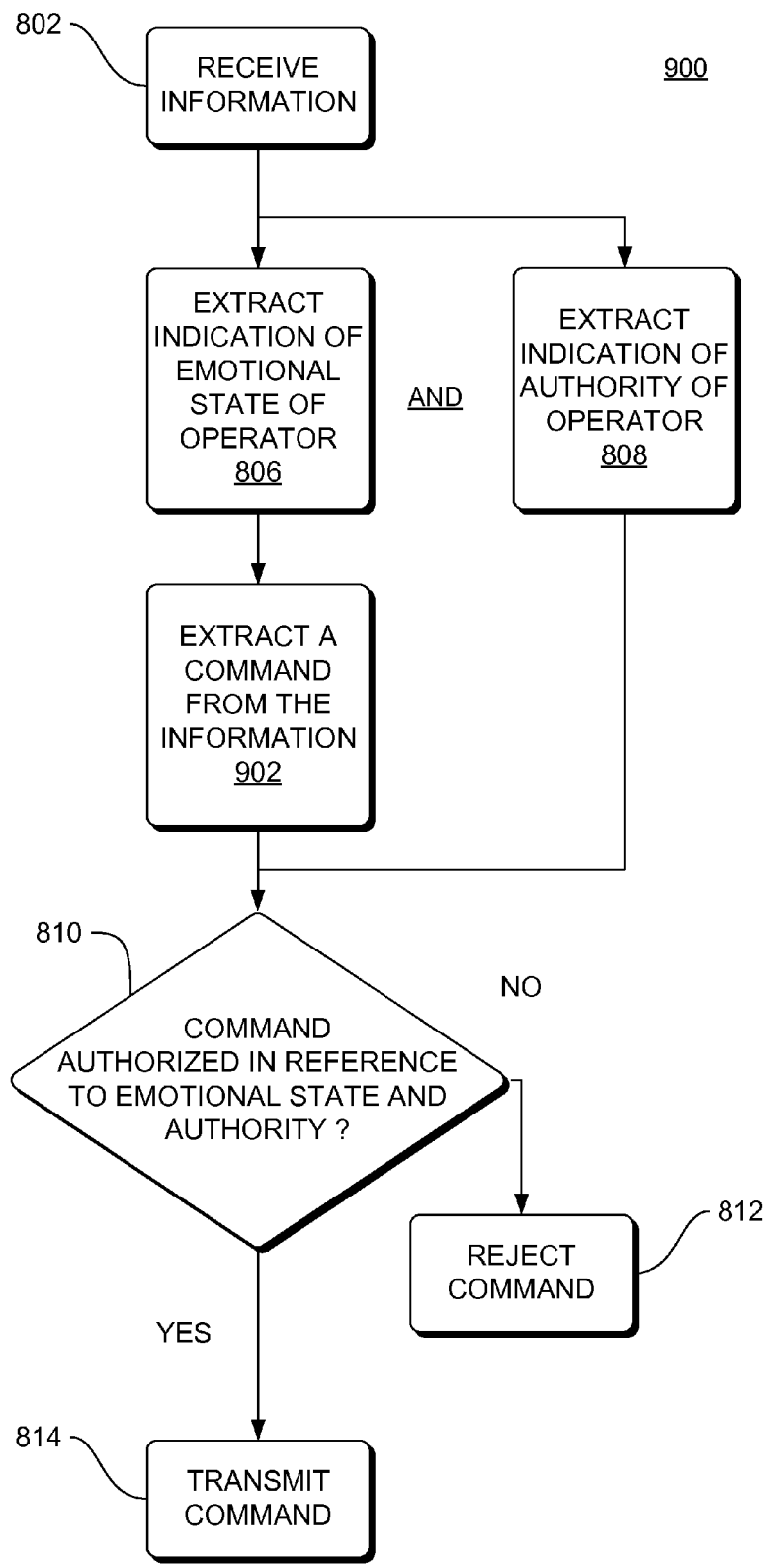
FIG. 9 is a flowchart of a method to control a patient-lifting-device, according to an implementation.

FIG. 9 is a flowchart of a method 900 to control a patient-lifting-device, according to an implementation. Method 900 receives information from a human and generates a command from the human information, in reference to authority of the human and the state of the mind of the human. Method 900 generates command(s) that are suitable to be processed by a processor in control of a patient-lifting-device. In some implementations, method 900 is performed by the command interface unit 102 and FIG. 1 and FIG. 2.

Method 900 includes receiving 802 information from one of a number of different communication devices. FIG. 5 describes some implementations of communication devices.

Method 900 includes processing the information by analyzing the information and extracting 808 from the information an indicator of the authority of the operator. In some embodiments, extracting an indication of authority of the operator includes identifying the operator. For example, where the information 802 is audio information from a human speaker, the identity of the human speaker is determined and the authority of that speaker is then determined. In some embodiments, the speech pattern of the human speaker is compared to a database of known humans. In method 900, the database is accessed and a comparison of the information 802 to the speech samples in the database is performed. When the comparing determines the identity of the human speaker, the authority of the identified human is accessed and used as the indicator of authority of the operator.

Method 900 includes processing the information by analyzing the information and extracting 902 a command from the information. Examples of the command include "move up" "move down" "move forward" and "move backward." Method 900 includes processing the information by analyzing and extracting 806 from the information indicators of the emotional state of the operator, indicators of the competency of the operator, and/or indicators of the state-of-mind of the operator.

In method 900, the command, the state-of-mind and the indicator of authority of the operator is analyzed 810 to an authority database to determine whether or not the command is authorized by the authority of the operator in consideration of the emotional state of the operator. If the command is not authorized by the authority and emotional state of the operator, the command is rejected 812. In some implementations, rejecting 812 the command can include transmitting a notice of an attempted unauthorized command to supervisory personnel or law enforcement agency. If the command is determined to be authorized, the command is transmitted 814 to the processor (e.g. 106 in FIG. 1) and the command 812 is performed by the patient-lifting-device. In some implementations, a log or journal of all extracted commands in action 902 and the determination 810 of the authority of the extracted commands is stored.

Method 900 provides command control of a patient-movement-actuator 114 through a variety of input mediums, such verbal audio input, hand-held keypad controllers synaptic activity sensor in reference or consideration to the authority and emotion, competency and state of mind of the operator from which the command is issued, with the added efficiency of not interpreting the command from the input information until after the authority and emotion, competency and state of mind of the operator, as represented in the input information, is evaluated. The multisensory command input of method 900 benefits people with physical difficulties by reducing if not completely eliminating the requirement to manually control the patient-movement-actuator 114.

Figure 10:
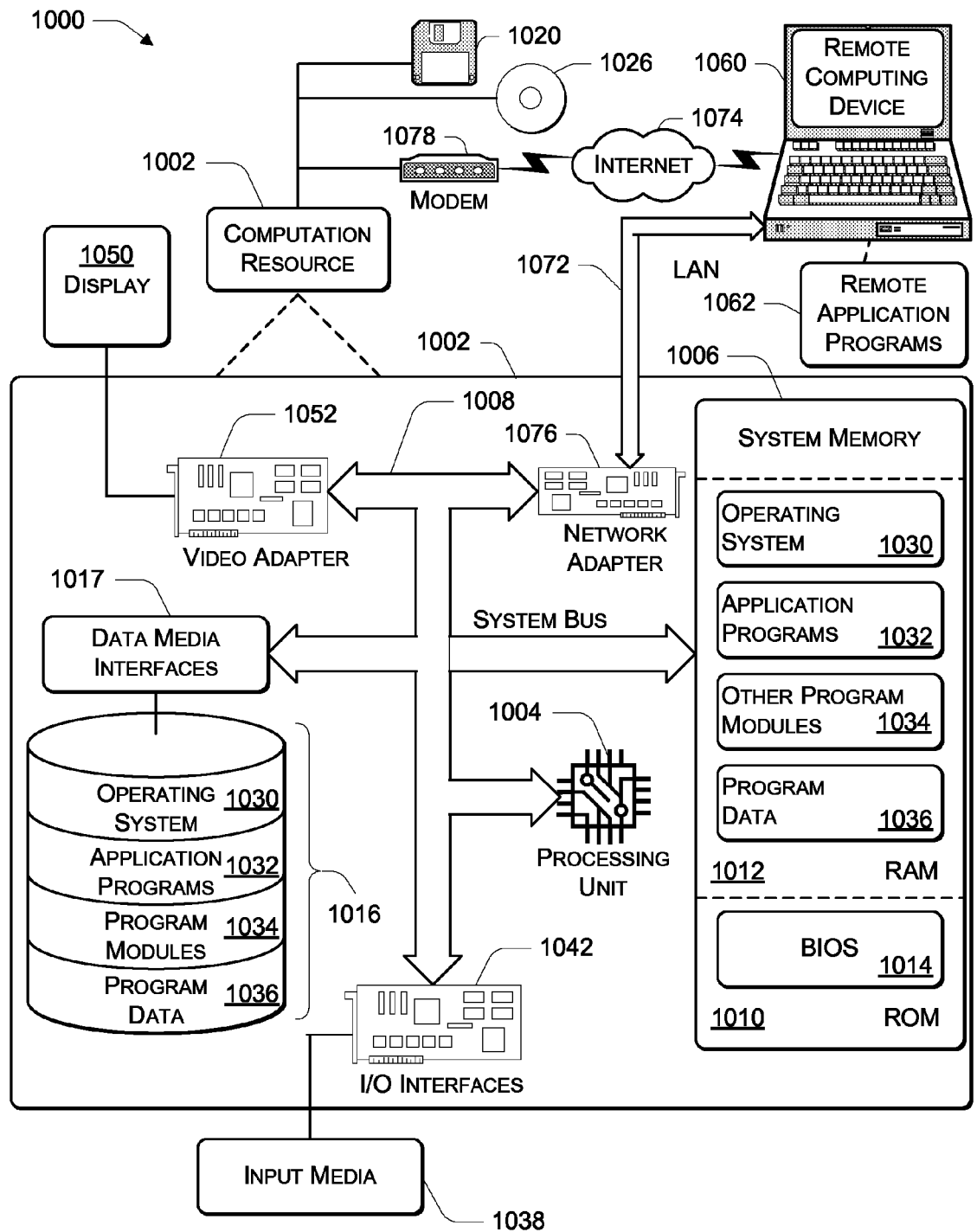
FIG. 10 illustrates an example of a computer environment useful in the context of the environments of FIG. 1-9, according to an implementation.

In some implementations, methods 800-900 are implemented as a sequence of instruction which, when executed by a processor, such as processor unit 1004 in FIG. 10, processor 106 in FIG. 1 and FIG. 2, or cause the processor to perform the respective method. In other implementations, methods 800-900 are implemented as a computer-accessible medium having executable instructions capable of directing a processor, such as processor unit 1004 in FIG. 10, to perform the respective method. In some implementations, methods 800-900 are implemented as a sequence of instructions which, when executed by a processor, such as microcontroller, processor or microprocessor 1102 in FIG. 11, cause the microcontroller, processor or microprocessor 1102 to perform the respective method. In other implementations, methods 800-900 are implemented as a computer-accessible medium having executable instructions capable of directing a processor, such as microcontroller, processor or microprocessor 1102 in FIG. 11, to perform the respective method. In varying implementations, the medium is a magnetic medium, an electronic medium, or an optical medium.

Hardware and Operating Environment

FIG. 10 is a block diagram of a hardware and operating environment 1000 in which different implementations can be practiced. The description of FIG. 10 provides an overview of computer hardware and a suitable computing environment in conjunction with which some implementations can be implemented. Implementations are described in terms of a computer executing computer-executable instructions. However, some implementations can be implemented entirely in computer hardware in which the computer-executable instructions are implemented in read-only memory. Some implementations can also be implemented in client/server computing environments where remote devices that perform tasks are linked through a communications network. Program modules can be located in both local and remote memory storage devices in a distributed computing environment.

FIG. 10 illustrates an example of a computer environment 1000 useful in the context of the environment of FIG. 1-9, in accordance with an implementation. The computer environment 1000 includes a computation resource 1002 capable of implementing the processes described herein. It will be appreciated that other devices can alternatively used that include more components, or fewer components, than those illustrated in FIG. 10.

The illustrated operating environment 1000 is only one example of a suitable operating environment, and the example described with reference to FIG. 10 is not intended to suggest any limitation as to the scope of use or functionality of the implementations of this disclosure. Other well-known computing systems, environments, and/or configurations can be suitable for implementation and/or application of the subject matter disclosed herein.

The computation resource 1002 includes one or more processors or processing units 1004, a system memory 1006, and a bus 1008 that couples various system components including the system memory 1006 to processor(s) 1004 and other elements in the environment 1000. The bus 1008 represents one or more of any of several types of bus structures, including a memory bus or memory controller, a peripheral bus, an accelerated graphics port and a processor or local bus using any of a variety of bus architectures, and can be compatible with SCSI (small computer system interconnect), or other conventional bus architectures and protocols.

The system memory 1006 includes nonvolatile read-only memory (ROM) 1010 and random access memory (RAM)

1012, which can or can not include volatile memory elements. A basic input/output system (BIOS) 1014, containing the elementary routines that help to transfer information between elements within computation resource 1002 and with external items, typically invoked into operating memory during start-up, is stored in ROM 1010.

The computation resource 1002 further can include a non-volatile read/write memory 1016, represented in FIG. 10 as a hard disk drive, coupled to bus 1008 via a data media interface 1017 (e.g., a SCSI, ATA, or other type of interface); a magnetic disk drive (not shown) for reading from, and/or writing to, a removable magnetic disk 1020 and an optical disk drive (not shown) for reading from, and/or writing to, a removable optical disk 1026 such as a CD, DVD, or other optical media.

The non-volatile read/write memory 1016 and associated computer-readable media provide nonvolatile storage of computer-readable instructions, data structures, program modules and other data for the computation resource 1002. Although the exemplary environment 1000 is described herein as employing a non-volatile read/write memory 1016, a removable magnetic disk 1020 and a removable optical disk 1026, it will be appreciated by those skilled in the art that other types of computer-readable media which can store data that is accessible by a computer, such as magnetic cassettes, FLASH memory cards, random access memories (RAMs), read only memories (ROM), and the like, can also be used in the exemplary operating environment.

A number of program modules can be stored via the non-volatile read/write memory 1016, magnetic disk 1020, optical disk 1026, ROM 1010, or RAM 1012, including an operating system 1030, one or more application programs 1032, other program modules 1034 and program data 1036. Examples of computer operating systems conventionally employed include the NUCLEUS® operating system, the LINUX® operating system, and others, for example, providing capability for supporting application programs 1032 using, for example, code modules written in the C++® computer programming language.

A user can enter commands and information into computation resource 1002 through input devices such as input media 1038 (e.g., keyboard/keypad, tactile input or pointing device, mouse, foot-operated switching apparatus, joystick, touchscreen or touchpad, microphone, antenna etc.). Such input devices 1038 are coupled to the processing unit 1004 through a conventional input/output interface 1042 that is, in turn, coupled to the system bus. A monitor 1050 or other type of display device is also coupled to the system bus 1008 via an interface, such as a video adapter 1052.

The computation resource 1002 can include capability for operating in a networked environment using logical connections to one or more remote computers, such as a remote computer 1060. The remote computer 1060 can be a personal computer, a server, a router, a network PC, a peer device or other common network node, and typically includes many or all of the elements described above relative to the computation resource 1002. In a networked environment, program modules depicted relative to the computation resource 1002, or portions thereof, can be stored in a remote memory storage device such as can be associated with the remote computer 1060. By way of example, remote application programs 1062 reside on a memory device of the remote computer 1060. The logical connections represented in FIG. 10 can include interface capabilities, e.g., such as interface capabilities in FIG. 5, a storage area network (SAN, not illustrated in FIG. 10), local area network (LAN) 1072 and/or a wide area network (WAN) 1074, but can also include other networks.

Such networking environments are commonplace in modern computer systems, and in association with intranets and the Internet. In certain implementations, the computation resource 1002 executes an Internet Web browser program (which can optionally be integrated into the operating system 1030), such as the "Internet Explorer®" Web browser manufactured and distributed by the Microsoft Corporation of Redmond, Wash.

When used in a LAN-coupled environment, the computation resource 1002 communicates with or through the local area network 1072 via a network interface or adapter 1076. When used in a WAN-coupled environment, the computation resource 1002 typically includes interfaces, such as a modem 1078, or other apparatus, for establishing communications with or through the WAN 1074, such as the Internet. The modem 1078, which can be internal or external, is coupled to the system bus 1008 via a serial port interface.

In a networked environment, program modules depicted relative to the computation resource 1002, or portions thereof, can be stored in remote memory apparatus. It will be appreciated that the network connections shown are exemplary, and other means of establishing a communications link between various computer systems and elements can be used.

A user of a computer can operate in a networked environment using logical connections to one or more remote computers, such as a remote computer 1060, which can be a personal computer, a server, a router, a network PC, a peer device or other common network node. Typically, a remote computer 1060 includes many or all of the elements described above relative to the computer 1000 of FIG. 10.

The computation resource 1002 typically includes at least some form of computer-readable media. Computer-readable media can be any available media that can be accessed by the computation resource 1002. By way of example, and not limitation, computer-readable media can comprise computer storage media and communication media.

Computer storage media include volatile and nonvolatile, removable and non-removable media, implemented in any method or technology for storage of information, such as computer-readable instructions, data structures, program modules or other data. The term "computer storage media" includes, but is not limited to, RAM, ROM, EEPROM, FLASH memory or other memory technology, CD, DVD, or other optical storage, magnetic cassettes, magnetic tape, magnetic disk storage or other magnetic storage devices, or any other media which can be used to store computer-intelligible information and which can be accessed by the computation resource 1002.

Communication media typically embodies computer-readable instructions, data structures, program modules or other data, represented via, and determinable from, a modulated data signal, such as a carrier wave or other transport mechanism, and includes any information delivery media. The term "modulated data signal" means a signal that has one or more of its characteristics set or changed in such a manner as to encode information in the signal in a fashion amenable to computer interpretation.

By way of example, and not limitation, communication media include wired media, such as wired network or direct-wired connections, and wireless media, such as acoustic, RF, infrared and other wireless media. The scope of the term computer-readable media includes combinations of any of the above.

The computer 1002 can function as one or more of the control segments, via implementation of the processes in FIGS. 8-9, respectively, as one or more computer program modules.

Figure 11:
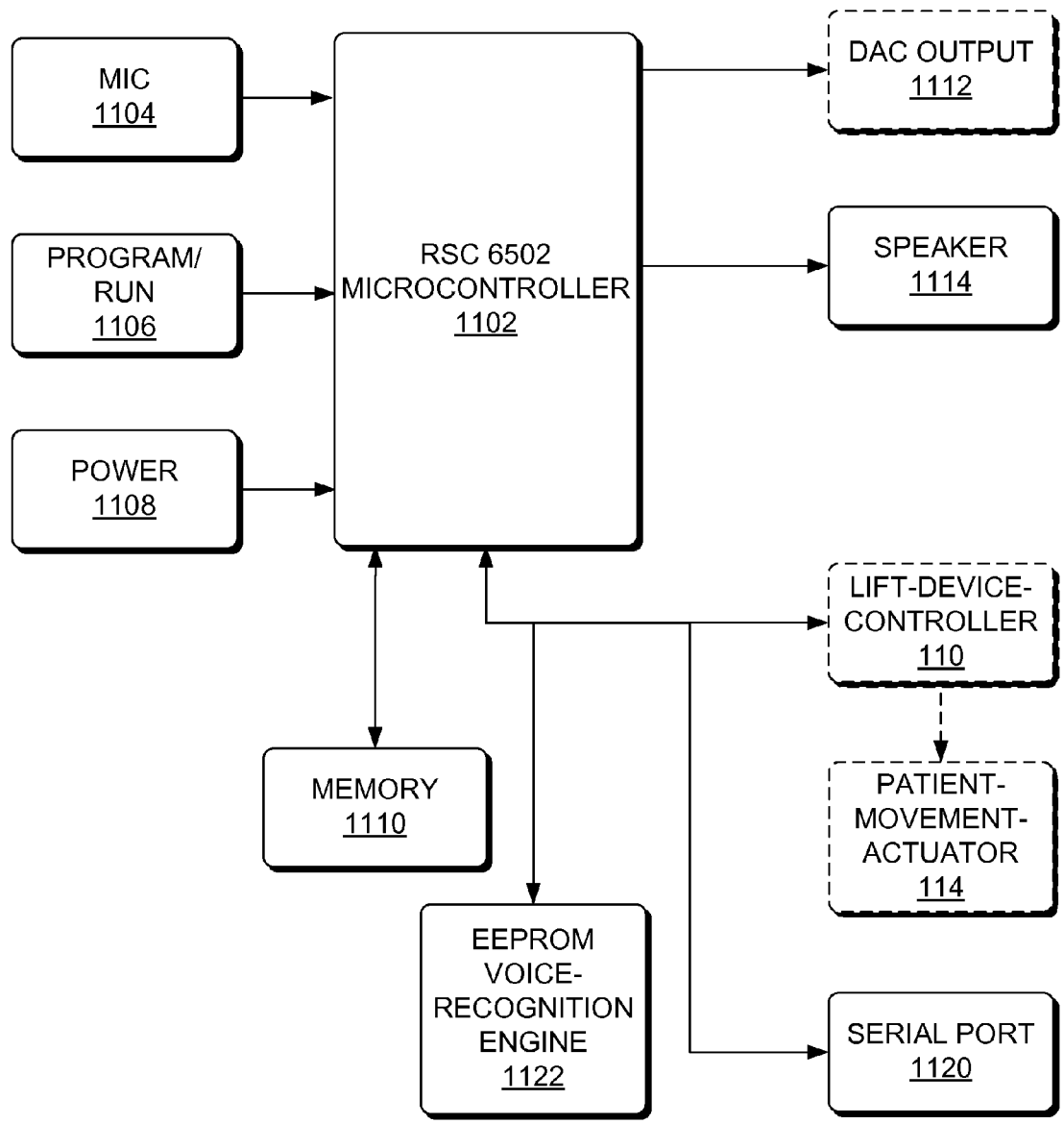
FIG. 11 is a block diagram of a voice-recognition unit for a patient-lifting-device, according to an implementation.

FIG. 11 is a block diagram of a voice-recognition apparatus 1100 to control a patient-lifting-device, according to an implementation. The voice-recognition apparatus 1100 is one implementation of voice-recognition unit 604 in FIG. 6. The voice-recognition apparatus 1100 receives input from any one of a number of input mediums, such as audio, and therefrom controls a patient-lifting-device. The voice-recognition apparatus 1100 can fit inside the housing of conventional patient-lifting-device and can communicate with and control conventional patient-lifting-device using the conventional existing electrical circuitry of patient-lifting-device. The voice-recognition apparatus 1100 helps improve control of the patient-lifting-device by receiving input from any one of a number of input mediums, such as audio. In the example of audio, the voice-recognition apparatus 1100 improves the ease and convenience with which an operator can control the patient-lifting-device by providing a voice interface to the patient-lifting-device. In general, the voice-recognition apparatus 1100 improves the ease and convenience with which an operator can control the patient-lifting-device by providing a command interface to the patient-lifting-device other than a handheld control device.

Voice-recognition apparatus 1100 includes a microcontroller, processor or microprocessor 1102. The microcontroller, processor or microprocessor 1102 is one example of the processor 106 in FIG. 1 and FIG. 2.

One example of the microcontroller, processor or microprocessor 1102 is RSC 6502 microcontroller. The 6502 is an 8-bit processor with a 16-bit address bus. The internal logic runs at the same speed as the external clock rate, and having clock speeds typically in the neighborhood of 1 or 2 MHz. The 6502 has a relatively simplistic state machine implemented by combinatorial (clockless) logic. A two phase clock (supplying two synchronizations per cycle) can thereby control the whole machine-cycle directly. The 6502 microcontroller is not sequenced by a microcode read-only-memory but uses a programmable logic array for instruction decoding and sequencing. Like most typical eight-bit microprocessors, the 6502 microcontroller does some limited overlapping of fetching and execution. The low clock frequency moderates the speed requirement of memory and peripherals attached to the 6502 microcontroller, as only about 50% of the clock cycle is available for memory access (due to the asynchronous design, this percentage varies strongly among chip versions). The 6502 microcontroller is minimalistically engineered and efficiently manufactured and therefore inexpensive. Like its precursor, the Motorola 6800 (but unlike Intel 8080 and similar microprocessors) the 6502 microcontroller has very few registers. The registers of the 6502 microcontroller include one 8-bit accumulator register (A), two 8-bit index registers (X and Y), an 8-bit processor status register (P), an 8-bit stack pointer (S), and a 16-bit program counter (PC). The subroutine call/scratchpad stack's address space is hardwired to memory page $01, i.e. the address range $0100-$01FF (256-511). Software access to the stack is performed via four implied addressing mode instructions whose functions are to push or pop (pull) the accumulator or the processor status register. The same stack is also used for subroutine calls via the JSR (Jump to Subroutine) and RTS (Return from Subroutine) instructions, and for interrupt handling. The 6502 microcontroller uses the index and stack registers effectively with several addressing modes, including a fast "direct page" or "zero page" mode, similar to that found on the PDP-8, that accessed memory locations from address 0 to 255 with a single 8-bit address (saving the cycle normally required to fetch the high-order byte of the address)—code for the 6502 use the zero page much as code for other processors would have used registers. Addressing modes also include implied (1 byte instructions); absolute (3 bytes); indexed absolute (3 bytes); indexed zero-page (2 bytes); relative (2 bytes); accumulator (1); indirect,x and indirect,y (2); and immediate (2). Absolute mode is a general-purpose mode. Branch instructions use a signed 8-bit offset relative to the instruction after the branch; the numerical range −128 . . . 127 therefore translates to 128 bytes backward and 127 bytes forward from the instruction following the branch (which is 126 bytes backward and 129 bytes forward from the start of the branch instruction). Accumulator mode uses the accumulator as an effective address, and did not need any operand data. Immediate mode uses an 8-bit literal operand. The indirect modes are useful for array processing and other looping. With the 5/6 cycle "(indirect),y" mode, the 8-bit Y register is added to a 16-bit base address in zero page, located by a single byte following the opcode. As the resulting address could be anywhere in the 16-bit memory range, the Y register is a true index register, as opposed to the 6800, which had one 16-bit address register. Incrementing the index register to walk the array byte-wise took only two additional cycles. With the less frequently used "(indirect,x)" mode the effective address for the operation is found at the zero page address formed by adding the second byte of the instruction to the contents of the X register. Using the indexed modes, the zero page effectively acted as a set of 128 additional (though very slow) address registers. The 6502 also includes a set of binary coded decimal (BCD) instructions, a feature normally implemented in software. Placing the CPU into BCD allowed numbers to be manipulated in base-10, with a set of conversion instructions to convert between base-10 and binary (base-2). For instance, with the "D" flag set, 99+1 would result in 00 and the carry flag being set. These instructions remove the need to convert numbers for display in the BASIC interpreter itself. However, this feature means other useful instructions can not be implemented easily, and is sometimes removed to make room for custom instructions. The RSC 6502 microcontroller is merely one example of microcontroller, processor or microprocessor that can be used in the voice-recognition apparatus 1100. The RSC 6502 microcontroller has been manufactured by Conexant Systems at 4000 MacArthur Boulevard, Newport Beach, Calif.

The microcontroller, processor or microprocessor 1102 is operably coupled to a voice-recognition apparatus 1100 and at least one microphone 504.

And some implementations, the microcontroller, processor or microprocessor 1102 is operably coupled to a program/run switch 1106 that is set to indicate the mode that the microcontroller, processor or microprocessor 1102 is operating. When the microcontroller, processor or microprocessor 1102 is being programmed, the program/run switch 1106 is set to program. When the microcontroller, processor or microprocessor 1102 is being run, the program/run switch 1106 is set to run.

The microcontroller, processor or microprocessor 1102 is operably coupled to a power input 1106.

In some implementations, the microcontroller, processor or microprocessor 1102 is operably coupled to a memory 1110 that stores data and programs. In some implementations, the microcontroller, processor or microprocessor 1102 is operably coupled to a digital-to-analog (DAC) converter that generates DAC output 1112. In some implementations, the microcontroller, processor or microprocessor 1102 is operably coupled to an audio speaker 1114.

In other implementations, the microcontroller, processor or microprocessor 1102 (microprocessor/microcontroller/processor) includes memory. In some implementations in which the microprocessor/microcontroller/processor 1102 includes memory, the microprocessor/microcontroller/processor 1102 provides an economical wireless voice control and communications system. The microprocessor/microcontroller/processor 1102 incorporates voice recognition, infrared (IR) and radio frequency (RF) wireless protocols including Zigbee and Bluetooth wireless protocols with positional awareness and a complex programmable logic device (CPLD) interface. The microprocessor/microcontroller/processor 1102 communicates with and controls multi-sensory controls for products from microwaves and washing machines to spacecraft. The microprocessor/microcontroller/processors 1102 are selected from both 16-bit and 32-bit devices. The microprocessor/microcontroller/processor 1102 having 16-bit radio-frequency (RF) interfaces are well-suited for applications such as wireless keyboard/mouse, wireless voice-over-IP (VoIP), remote controls, wireless gaming accessories, home and building automation applications such as alarm and security systems, automatic meter reading systems, active radio-frequency identification (RFID) systems and other monitoring and control systems.

Microprocessor/microcontroller/processors 1102 having 32-bit word-length include high performance integrated peripherals designed for real-time control applications. An optimized core of the microprocessor/microcontroller/processor 1102 performs multiple complex control algorithms at speeds necessary for demanding control applications. Integrated peripherals such as a 16-channel, 12-bit analog-to-digital conversion (ADC) running at up to 12.5 megasamples per second and high resolution pulse-width modulation (PWM) modules with 150 picosecond resolution provide sufficient bandwidth for communication with analog devices. Further including the serial peripheral interface (SPI), universal asynchronous receiver/transmitter (UART), inter-IC (I2C), campus area network (CAN), and multi-channel buffered serial port (McBSP) communication peripherals provides device control on a single microprocessor/microcontroller/processor 1102. Applications include appliances, alternating current/direct current (AC/DC), direct current/alternating (DC/AC) and direct current/direct current (DC/DC) digital power supplies, solar inverters, digital motor control, and power line communication.

The microcontroller, processor or microprocessor 1102 can implement the components in FIG. 3 and FIG. 4 and can perform actions 804, 806, 808, 810, 812 and 814 in FIG. 8 and action 902 in FIG. 9.

In some implementations, the microcontroller, processor or microprocessor 1102 is operably coupled to a lift-device-controller 110 and the lift-device-controller 110 is electrically coupled to at least one patient-movement-actuator 114. In some implementations, the microcontroller, processor or microprocessor 1102 is electrically coupled directly to the patient-movement-actuator 114. Examples of the patient-lifting-device include the two dimensional patient-lifting-device 1200 in FIG. 12 and a one dimensional patient-lifting-device (not shown). One implementation of the patient-movement-actuator 114 for a two dimensional patient-lifting-device (e.g. the two dimensional patient-lifting-device 1200 in FIG. 12) implements a double-pole-double-throw (DPDT) relay for each direction of movement of the two dimensional patient-lifting-device. The lift-device-controller 110 in FIG. 11 is one example of lift-device-controller 110 in FIG. 1 and FIG. 2. The lift-device-controller 110 and the patient-movement-actuator 114 are not a part of the voice-recognition apparatus 1100 as indicated by the dashed border lines of the lift-device-controller 110 and the patient-movement-actuator 114, but the lift-device-controller 110 and the patient-movement-actuator 114 is shown in the FIG. 11 to provide a more comprehensive view of the configuration and interoperability of the voice-recognition apparatus 1100, the lift-device-controller 110 and the patient-movement-actuator 114.

In some implementations, the microcontroller, processor or microprocessor 1102 is operably coupled to a serial port 1120 through which program instructions can be loaded onto the microcontroller, processor or microprocessor 1102.

In some implementations, the microcontroller, processor or microprocessor 1102 is operably coupled to a nonvolatile memory that stores a voice-recognition engine. In the implementation shown in FIG. 11, the nonvolatile memory is electrically erasable programmable read only memory (EEPROM) 1122. The voice-recognition engine 1122 includes a predefined set of functions that are called during voice-recognition operations.

The illustrated operating environment 1100 is only one example of a suitable operating environment, and the example described with reference to FIG. 11 is not intended to suggest any limitation as to the scope of use or functionality of the implementations of this disclosure. Other well-known computing systems, environments, and/or configurations can be suitable for implementation and/or application of the subject matter disclosed herein.

Voice-recognition apparatus 1100 provides verbal command control of a patient-movement-actuator 114. The verbal command input benefits people with physical difficulties by reducing if not completely eliminating the requirement to manually control the patient-movement-actuator 114.

Figure 12:
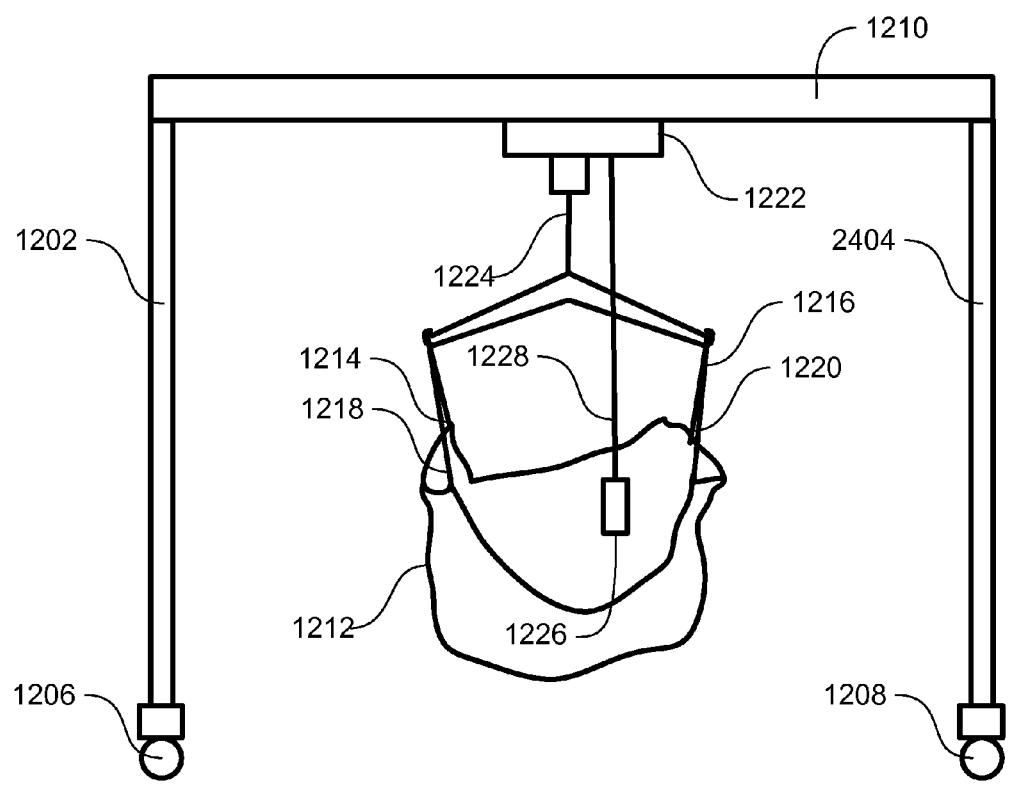
FIG. 12 is a block diagram of a two dimensional patient-lifting-device, according to an implementation that is specifically adapted for lifting a patient out of bed.

FIG. 12 is a block diagram of a two dimensional patient-lifting-device 1200, according to an implementation that is specifically adapted for lifting a patient out of a bed. The two dimensional patient-lifting-device 1200 in FIG. 12 is one example of patient-lifting devices.

Patient-lifting-device 1200 includes vertical main supports 1202 and 1204 that are optionally supported by wheels 1206 and 1208 for movement on the ground. Patient-lifting-device 1200 also includes a horizontal support 1210 that is fixedly attached to the vertical main supports 1202 and 1204. In the implementation shown in FIG. 12, a seat or hammock 1212 is attached to the horizontal support 1210 via lines 1214, 1216, 1218 and 1220, although other implementations of the seat or hammock 1212 are well-known. An electric or hydraulic control box 1222 is slidably attached to the horizontal support 1210 through a rail (not shown) and the lines 1214, 1216, 1218 and 1220 are attached to the control box 1222 through a line 1224. The control box 1222 causes the line 1224 to be extended or retracted. A patient is placed in the seat or hammock 1212 for movement. As the line 1224 is extended, the hammock or seat 1212 is lowered downward, thus causing the patient in the hammock or seat 1212 to move downward. As the line 1224 is retracted, the seat or hammock 1212 is moved upward, thus causing the patient in the hammock or seat 1212 to move upwards. In addition the control box 1222 is operable to move horizontally along the horizontal support 1210 on the rail.

In some implementations, the control box 1222 includes various apparatus and systems described in this application that provide control of the patient-lifting-device 1200 from various stimulus such as audio voice input. Examples of the various apparatus and systems that are included in the control box 1222 include the command interface unit 102, processor 106, lift-device-controller 110 and/or patient-movement-actuator 114 in FIG. 1 and FIG. 2; and control box 1222 can be operably coupled to the keyboard data receiver 502, voice data receiver 504, a synaptic activity sensor 506 in FIG. 5, the microphone 602 and or voice-recognition unit 604 in FIG. 6, the device configuration user interface 702 and/or the modifiable logic circuit 704 in FIG. 7, the electrical devices in FIGS. 10-11 and 13, and other tangible systems that perform methods 300, 400, 800 and/or 900.

In some implementations, the two dimensional patient-lifting-device 1200 includes a hand-held keypad controller 1226 that includes buttons for up, down, forward, backward and stop 1226 that is electrically coupled to the patient-movement-actuator 114 in the control box 1222 via a line 1228, the hand-held keypad controller 1226 providing signals that direct movement of the line 1224 and movement of the control box 1222 along the horizontal support 1210. In some implementations, control initiated from the hand-held keypad controller 1226 overrides control initiated from other input means.

In some implementations, the only input devices for commands in the patient-lifting-device 1200 are a microphone 602 operably coupled to a voice data receiver 504; and hand-held keypad controller 1226. In such implementations, a keyboard data receiver and a synaptic activity sensor 506 are not included in the patient-lifting-device 1200.

Some implementations of the two dimensional patient-lifting-device 1200 include a charging unit (not shown) in the horizontal support 1210 and/or the control box 1222 to provide power for recharging a battery. The battery can be mounted either in the control box 1222 or the horizontal support 1210. The charging unit is electrically coupled to a power cord having male prongs on the other end from the charging unit that are suitable to plug into a standard residential electrical wall outlet female receptacle.

Some implementations of the two dimensional patient-lifting-device 1200 are a portable patient-lifting-device that fits in doorways.

Figure 13:
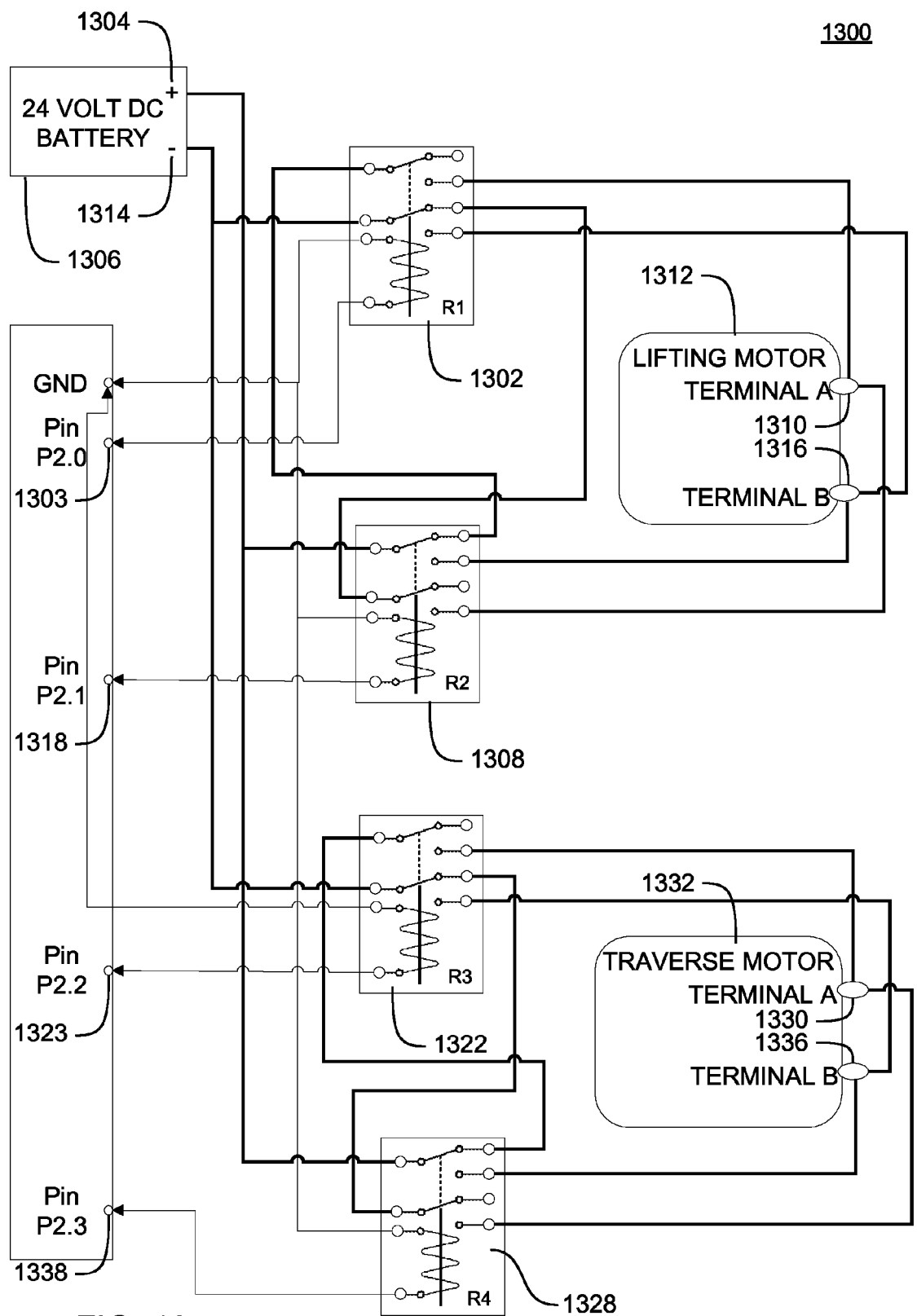
FIG. 13 is a block diagram of a patient-movement-actuator of a patient-lifting-device, according to an implementation using DPTD relays.

FIG. 13 is a block diagram of a patient-movement-actuator 1300 of a patient-lifting-device, according to an implementation using DPTD relays. Patient-movement-actuator 1300 is one implementation of the patient-movement-actuator 114 in FIGS. 1, 2 and 11 for a two dimensional patient-lifting-device, such as two dimensional patient-lifting-device 1200 in FIG. 12, that implements a normally-open double-pole-double-throw (DPDT) relay for each direction of movement of the two dimensional patient-lifting-device. Two-dimensional movement consists of movement in four directions, hence patient-movement-actuator 1300 consists of four normally-open DTDT relays. Other implementations of patient-movement-actuator 1300 that do not have the safety features of patient-movement-actuator 1300 implement single-pole-single-throw (SPST) relays.

To command movement in a particular direction, the corresponding relay is actuated. To actuate the patient-lifting-device in an upward direction, DPDT relay 1302 is actuated by setting voltage "high" (e.g. 3 volts) on pin "P2.0" 1303. When DPDT relay 1302 is actuated, the normally-open DPDT relay 1302 is closed, thereupon a positive electric current will flow from the positive terminal 1304 of the 24 volt DC battery 1306, through DPDT relay 1308, and through DPDT relay 1302 to Terminal A 1310 of lifting motor 1312 and also when DTDT relay 1302 is actuated, a negative electric current will flow from the negative terminal 1314 of the 24 volt DC battery 1306, through DPDT relay 1302 to Terminal B 1316 of lifting motor 1312, thus providing electric current to lifting motor 1312 in a polarity that will retract a line coupled to the lifting motor 1312, thereupon lifting the seat or hammock 2612.

To actuate the patient-lifting-device in a downward direction, DPDT relay 1308 is actuated by setting voltage "high" (e.g. 3 volts) on pin "P2.1" 1318. When DPDT relay 1308 is actuated, the normally-open DPDT relay 1308 becomes closed, thereupon a negative electric current will flow from the negative terminal 1314 of the 24 volt DC battery 1306, through DPDT relay 1302, and through DPDT relay 1308 to Terminal A 1310 of lifting motor 1312 and also when DTDT relay 1308 is actuated, a positive electric current will flow from the positive terminal 1304 of the 24 volt DC battery 1306, through DPDT relay 1308 to Terminal B 1316 of lifting motor 1312, thus providing electric current to lifting motor 1312 in a polarity that will extend a line coupled to the lifting motor 1312, thereupon lowering the seat or hammock 2612.

Please note the safety feature in the serial wiring of DTDT relay 1302 and DPDT relay 1308. The safety feature lies in that positive electric current will flow from the positive terminal 1304 of the 24 volt DC battery 1306, through DPDT relay 1308, and through DPDT relay 1302 to Terminal A 1310 of lifting motor 1312 when DPDT relay 1308 is not actuated. Positive electric current will not flow from the positive terminal 1304 of the 24 volt DC battery 1306, through DPDT relay 1308, and through DPDT relay 1302 to Terminal A 1310 of lifting motor 1312 when DPDT relay 1308 is actuated. Therefore, if somehow both DPDT relay 1302 and DPDT relay 1308 are simultaneously actuated, no current will flow to the lifting motor 1312, thus preventing both positive electric current and negative electric from simultaneously flowing to Terminal A 1310 of lifting motor 1312 and preventing both positive electric current and negative electric from simultaneously flowing to Terminal B 1316 of lifting motor 1312.

Other implementations use other power sources in place of the 24 volt DC battery 1306.

To actuate the patient-lifting-device in a forward traversal direction, DPDT relay 1322 is actuated by setting voltage "high" (e.g. 3 volts) on pin "P2.2" 1323. When DPDT relay 1322 is actuated, the normally-open DPDT relay 1322 is closed, thereupon a positive electric current will flow from the positive terminal 1304 of the 24 volt DC battery 1306, through DPDT relay 1328, and through DPDT relay 1322 to Terminal A 1330 of traversing motor 1332 and also when DTDT relay 1322 is actuated, a negative electric current will flow from the negative terminal 1334 of the 24 volt DC battery 1306, through DPDT relay 1322 to Terminal B 1336 of traversing motor 1332, thus providing electric current to traversing motor 1332 in a polarity that will traverse in a forward direction the line coupled to the traversing motor 1332, thereupon moving the seat or hammock 2612 forward.

To actuate the patient-lifting-device in a backward direction, DPDT relay 1328 is actuated by setting voltage "high" (e.g. 3 volts) on pin "P2.3" 1338. When DPDT relay 1328 is actuated, the normally-open DPDT relay 1328 becomes closed, thereupon a negative electric current will flow from the negative terminal 1334 of the 24 volt DC battery 1306, through DPDT relay 1322, and through DPDT relay 1328 to Terminal A 1330 of traversing motor 1332 and also when DTDT relay 1328 is actuated, a positive electric current will flow from the positive terminal 1304 of the 24 volt DC battery 1306, through DPDT relay 1328 to Terminal B 1336 of traversing motor 1332, thus providing electric current to traversing motor 1332 in a polarity that will traverse in a backward direction the line coupled to the traversing motor 1332, thereupon lowering the seat or hammock 2612.

Please note the safety feature in the serial wiring of DTDT relay 1322 and DPDT relay 1328. The safety feature lies in that positive electric current will flow from the positive terminal 1304 of the 24 volt DC battery 1306, through DPDT relay 1328, and through DPDT relay 1322 to Terminal A 1330 of traversing motor 1332 when DPDT relay 1328 is not actuated. Positive electric current will not flow from the positive terminal 1304 of the 24 volt DC battery 1306, through DPDT relay 1328, and through DPDT relay 1322 to Terminal A 1330 of traversing motor 1332 when DPDT relay 1328 is actuated. Therefore, if somehow both DPDT relay 1322 and DPDT relay 1328 are simultaneously actuated, no current will flow to the traversing motor 1332, thus preventing both positive electric current and negative electric from simultaneously flowing to Terminal A 1330 of traversing motor 1332 and preventing both positive electric current and negative electric from simultaneously flowing to Terminal B 1336 of traversing motor 1332.

A DPDT relay consists of two separate switches that operate at the same time, each one with normally open and normally closed contact through a common connector. Each of the two contacts on the switch can be routed in different ways, depending on the position of the switch. An example of a switch is a mini-toggle switch or a switch using a push or pull control.

DPDT relay switches commonly use polarity reversal. That is why some variations of the DPDT relay, such as the cross-over switches, are internally wired for that purpose. The cross-over switches have only four terminals or connections, as opposed to six on a DPDT relay. Two connections are used for the outputs and the other two for the inputs. The switch then selects either normal or reversed polarity when connected to any direct current source such as a battery.

A DPDT relay has a single coil with two arms that move simultaneously. Inside of the DPDT relay, there are two separate single-pole-double-throw (SPDT) switch mechanisms.

In some implementations of a two-dimensional patient-lifting-device, a control line that is associated with upward movement from a voice-recognition apparatus and a control line that is associated with upward movement from a hand-held keypad controller are both electrically coupled to pin "P2.0" 1303, a control line that is associated with downward movement from a voice-recognition apparatus and a control line that is associated with downward movement from a hand-held keypad controller are both electrically coupled to pin "P2.1" 1318, a control line that is associated with forward movement from a voice-recognition apparatus and a control line that is associated with forward movement from a hand-held keypad controller are both electrically coupled to pin "P2.1" 1323, and a control line that is associated with backward movement from a voice-recognition apparatus and a control line that is associated with backward movement from a hand-held keypad controller are both electrically coupled to pin "P2.2" 1328.

Conclusion

An omni-input patient lifting command system is described. A technical effect of the system is filtering and/or suppression of background noise of audio command input. A technical effect of the system is transforming multisensory input into control signals for a patient-lifting-device. A technical effect of the system is electrical control of a patient-lifting-device in reference to commands received from voice input. Although specific implementations are illustrated and described herein, it will be appreciated by those of ordinary skill in the art that any arrangement which is calculated to achieve the same purpose may be substituted for the specific implementations shown. This application is intended to cover any adaptations or variations. One of ordinary skill in the art will appreciate that implementations can be made in software implementation or any other hardware implementation that provides the required function.

In particular, one of skill in the art will readily appreciate that the names of the methods and apparatus are not intended to limit implementations. Furthermore, additional methods and apparatus can be added to the components, functions can be rearranged among the components, and new components to correspond to future enhancements and physical devices used in implementations can be introduced without departing from the scope of implementations. One of skill in the art will readily recognize that implementations are applicable to future patient-lifting-devices and different command input devices.

The terminology used in this application meant to include all patient-lifting-devices, and voice recognition systems and alternate technologies which provide the same functionality as described herein.

In some aspects, an apparatus includes a patient-movement-actuator that is operable to receive at least one electrical signal, a lift-device-controller that is electrically coupled to the patient-movement-actuator and that is operable to receive at least one instruction and that is operable to generate the at least one electrical signal from the at least one instruction, a processor that is electrically coupled to the lift-device-controller and that is operable to receive a command and that is operable to generate the at least one instruction from the command in response to a sufficient authority, a sufficient level of emotional state, a sufficient competency and a sufficient state-of-mind of the command, a plurality of input devices, and a field-programmable gate array that is operable to receive multisensory digital audio input from the plurality of input devices, filter environment background noise from the multisensory digital audio input, extract from the filtered multisensory digital audio input the command relevant to the patient-movement-actuator, extract from the filtered multisensory digital audio input an indicator of an authority of the multisensory digital audio input, identify an authority associated with the multisensory digital audio input from the indicator of the authority, determine indicators of the emotional state, competency and state-of-mind in the multisensory digital audio input, and analyze the indicators of the emotional state, competency and state-of-mind associated with the multisensory digital audio input for a sufficient level of emotional state, competency and state-of-mind that is required by the command. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, identify the authority includes compare a speech pattern of a human speaker to a database of known humans, and determine an identity of the human speaker, yielding the authority of the identified human.

In some aspects, an apparatus includes a plurality of input devices, and a field-programmable gate array that is operable to receive multisensory digital audio input from the plurality of input devices, filter environment background noise from the multisensory digital audio input, extract from the filtered multisensory digital audio input the command relevant to a patient-movement-actuator, extract from the filtered multisensory digital audio input an indicator of an authority of the multisensory digital audio input, identify an authority associated with the multisensory digital audio input from the indicator of the authority, determine indicators of the emotional state, competency and state-of-mind in the multisensory digital audio input, and analyze the indicators of the emotional state, competency and state-of-mind associated with the multisensory digital audio input for a sufficient level of emotional state, competency and state-of-mind that is required by the command. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, identify the authority includes compare a speech pattern of a human speaker to a database of known humans, and determine an identity of the human speaker, yielding the authority of the identified human. Some implementations include a patient-movement-actuator that is operable to receive at least one electrical signal, a lift-device-controller that is electrically coupled to the patient-movement-actuator and that is operable to receive at least one instruction and that is operable to generate the at least one electrical signal from the at least one instruction, and a processor that is electrically coupled to the lift-device-controller and that is operable receive a command and that is operable to generate the at least one instruction from the command in response to a sufficient authority, a sufficient level of emotional state, a sufficient competency and a sufficient state-of-mind of the command.

In some aspects, an apparatus includes a plurality of input devices, and a field-programmable gate array that is operable to receive multisensory input from the plurality of input devices, filter environment background noise from the multisensory input, extract from the filtered multisensory input a command relevant to a patient-movement-actuator, extract from the filtered multisensory input an indicator of an authority of the multisensory input, identify an authority associated with the multisensory input from the indicator of the authority, determine indicators of the emotional state, competency and state-of-mind in the multisensory input, and analyze the indicators of the emotional state, competency and state-of-mind associated with the multisensory input for a sufficient level of emotional state, competency and state-of-mind that is required by the command. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, identify the authority includes compare a speech pattern of a human speaker to a database of known humans, and determine an identity of the human speaker, yielding the authority of the identified human. Some implementations include a processor that is electrically coupled to the field-programmable gate array, the processor being operable receive a command and the processor being operable to generate at least one instruction from the command in response to a sufficient authority, a sufficient level of emotional state, a sufficient competency and a sufficient state-of-mind of the command. Some implementations include a patient-movement-actuator that is operable to receive at least one electrical signal, and a lift-device-controller that is electrically coupled to the patient-movement-actuator and that is operable to receive the at least one instruction and that is operable to generate the at least one electrical signal from the at least one instruction. In some implementations, the multisensory input includes multisensory input.

In some aspects, an apparatus includes a plurality of input devices, and a field-programmable gate array that is operable to receive multisensory input from the plurality of input devices, extract from the multisensory input a command relevant to a patient-movement-actuator, extract from the multisensory input an indicator of an authority of the multisensory input, identify an authority associated with the multisensory input from the indicator of the authority, determine indicators of the emotional state, competency and state-of-mind in the multisensory input, and analyze the indicators of the emotional state, competency and state-of-mind associated with the multisensory input for a sufficient level of emotional state, competency and state-of-mind that is required by the command. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, identify the authority includes compare a speech pattern of a human speaker to a database of known humans, and determine an identity of the human speaker, yielding the authority of the identified human. Some implementations include a processor that is electrically coupled to the field-programmable gate array, the processor being operable receive a command and the processor being operable to generate at least one instruction from the command in response to a sufficient authority, a sufficient level of emotional state, a sufficient competency and a sufficient state-of-mind of the command. Some implementations include a patient-movement-actuator that is operable to receive at least one electrical signal, and a lift-device-controller that is electrically coupled to the patient-movement-actuator and that is operable to receive the at least one instruction and that is operable to generate the at least one electrical signal from the at least one instruction. In some implementations, the multisensory input includes multisensory digital audio input. In some implementations, the field-programmable gate array is operable to filter environment background noise from the multisensory input.

In some aspects, an apparatus includes a plurality of input devices, and a field-programmable gate array that is operable to receive multisensory input from the plurality of input devices, extract from the multisensory input a command relevant to a patient-movement-actuator, determine indicators of authority, emotional state, competency and state-of-mind in the multisensory input, and analyze the indicators of the authority, emotional state, competency and state-of-mind associated for sufficient levels of authority, emotional state, competency and state-of-mind that is required by the command. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, determine the authority includes compare a speech pattern of a human speaker to a database of known humans, and determine an identity of the human speaker, yielding the authority of the identified human. Some implementations include a processor that is electrically coupled to the field-programmable gate array, the processor being operable receive a command and the processor being operable to generate at least one instruction from the command in response to a sufficient authority, a sufficient level of emotional state, a sufficient competency and a sufficient state-of-mind of the command. Some implementations include a patient-movement-actuator that is operable to receive at least one electrical signal, and a lift-device-controller that is electrically coupled to the patient-movement-actuator and that is operable to receive the at least one instruction and that is operable to generate the at least one electrical signal from the at least one instruction. In some implementations, the multisensory input includes multisensory digital audio input. In some implementations, the field-programmable gate array is operable to filter environment background noise from the multisensory input. In some implementations, the field-programmable gate array is operable to extract from the multisensory input an indicator of an authority of the multisensory input, and identify an authority associated with the multisensory input from the indicator of the authority.

In some aspects, an apparatus includes a plurality of input devices, a field-programmable gate array that is operable to receive multisensory input from the plurality of input devices, extract from the multisensory input a command relevant to a patient-movement-actuator, determine indicators of authority, emotional state, competency and state-of-mind in the multisensory input, and analyze the indicators of the authority, emotional state, competency and state-of-mind associated for sufficient levels of authority, emotional state, competency and state-of-mind that is required by the command, and a transmitter of the command to the patient-movement-actuator in response to sufficient levels of authority, emotional state, competency and state-of-mind that is required by the command. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, identify the authority includes compare a speech pattern of a human speaker to a database of known humans, and determine an identity of the human speaker, yielding the authority of the identified human. Some implementations include a processor that is electrically coupled to the field-programmable gate array, the processor being operable receive a command and the processor being operable to generate at least one instruction from the command in response to a sufficient authority, a sufficient level of emotional state, a sufficient competency and a sufficient state-of-mind of the command. Some implementations include a patient-movement-actuator that is operable to receive at least one electrical signal, and a lift-device-controller that is electrically coupled to the patient-movement-actuator and that is operable to receive the at least one instruction and that is operable to generate the at least one electrical signal from the at least one instruction. In some implementations, the multisensory input includes multisensory digital audio input. In some implementations, the field-programmable gate array is operable to filter environment background noise from the multisensory input. In some implementations, the field-programmable gate array is operable to extract from the multisensory input an indicator of an authority of the multisensory input, and identify an authority associated with the multisensory input from the indicator of the authority.

In some aspects, an apparatus includes a plurality of input devices, a field-programmable gate array that is operable to receive multisensory input from the plurality of input devices, extract from the multisensory input a command relevant to a patient-movement-actuator, and analyze indicators of authority, emotional state, competency and state-of-mind for sufficient levels of authority, emotional state, competency and state-of-mind that is required by the command, and a transmitter of the command to the patient-movement-actuator in response to sufficient levels of authority, emotional state, competency and state-of-mind that is required by the command. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, the field-programmable gate array is operable to extract from the multisensory input an indicator of an authority of the multisensory input, and identify an authority associated with the multisensory input from the indicator of the authority. In some implementations, identify the authority includes compare a speech pattern of a human speaker to a database of known humans, and determine an identity of the human speaker, yielding the authority of the identified human. Some implementations include a processor that is electrically coupled to the field-programmable gate array, the processor being operable receive a command and the processor being operable to generate at least one instruction from the command in response to a sufficient authority, a sufficient level of emotional state, a sufficient competency and a sufficient state-of-mind of the command. Some implementations include a patient-movement-actuator that is operable to receive at least one electrical signal, and a lift-device-controller that is electrically coupled to the patient-movement-actuator and that is operable to receive the at least one instruction and that is operable to generate the at least one electrical signal from the at least one instruction. In some implementations, the multisensory input includes multisensory digital audio input. In some implementations, the field-programmable gate array is operable to filter environment background noise from the multisensory input. In some implementations, the field-programmable gate array is operable to determine indicators of authority, emotional state, competency and state-of-mind in the multisensory input.

In some aspects, an apparatus includes a plurality of input devices, a field-programmable gate array that is operable to receive multisensory input from the plurality of input devices, and extract from the multisensory input a command relevant to a patient-movement-actuator, and a transmitter of the command to the patient-movement-actuator. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, the field-programmable gate array is operable to extract from the multisensory input an indicator of an authority of the multisensory input, and identify an authority associated with the multisensory input from the indicator of the authority. In some implementations, identify the authority includes compare a speech pattern of a human speaker to a database of known humans, and determine an identity of the human speaker, yielding the authority of the identified human. Some implementations include a processor that is electrically coupled to the field-programmable gate array, the processor being operable to receive the command and the processor being operable to generate at least one instruction from the command in response to a sufficient authority, a sufficient level of emotional state, a sufficient competency and a sufficient state-of-mind of the command. Some implementations include a patient-movement-actuator that is operable to receive at least one electrical signal, and a lift-device-controller that is electrically coupled to the patient-movement-actuator and that is operable to receive the at least one instruction and that is operable to generate the at least one electrical signal from the at least one instruction. In some implementations, the multisensory input includes multisensory digital audio input. In some implementations, the field-programmable gate array is operable to filter environment background noise from the multisensory input. In some implementations, the field-programmable gate array is operable to determine indicators of authority, emotional state, competency and state-of-mind in the multisensory input. In some implementations, the field-programmable gate array is operable to analyze the indicators of the authority, emotional state, competency and state-of-mind associated for sufficient levels of authority, emotional state, competency and state-of-mind that is required by the command. In some implementations, the transmitter includes a transmitter of the command to the patient-movement-actuator in response to sufficient levels of authority, emotional state, competency and state-of-mind that is required by the command.

In some aspects, an apparatus includes a plurality of input devices, a computer-accessible medium that is operable to receive multisensory input from the plurality of input devices, and extract from the multisensory input a command relevant to a patient-movement-actuator, and a transmitter of the command to the patient-movement-actuator. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, the field-programmable gate array is operable to extract from the multisensory input an indicator of an authority of the multisensory input, and identify an authority associated with the multisensory input from the indicator of the authority. In some implementations, identify the authority includes compare a speech pattern of a human speaker to a database of known humans, and determine an identity of the human speaker, yielding the authority of the identified human. Some implementations include a processor that is electrically coupled to the computer-accessible medium, the processor being operable to receive a command and the processor being operable to generate at least one instruction from the command in response to a sufficient authority, a sufficient level of emotional state, a sufficient competency and a sufficient state-of-mind of the command. Some implementations include a patient-movement-actuator that is operable to receive at least one electrical signal, and a lift-device-controller that is electrically coupled to the patient-movement-actuator and that is operable to receive the at least one instruction and that is operable to generate the at least one electrical signal from the at least one instruction. In some implementations, the multisensory input includes multisensory digital audio input. In some implementations, the computer-accessible medium is operable to filter environment background noise from the multisensory digital audio input. In some implementations, the computer-accessible medium is operable to determine indicators of authority, emotional state, competency and state-of-mind in the multisensory digital audio input. In some implementations, the computer-accessible medium is operable to analyze the indicators of the authority, emotional state, competency and state-of-mind associated for sufficient levels of authority, emotional state, competency and state-of-mind that is required by the command. In some implementations, the transmitter includes a transmitter of the command to the patient-movement-actuator in response to sufficient levels of authority, emotional state, competency and state-of-mind that is required by the command. In some implementations, the computer-accessible medium includes a field-programmable gate array.

In some aspects, an apparatus includes a plurality of input devices, a receiver of multisensory input from the plurality of input devices, an extractor from the multisensory input a command relevant to a patient-movement-actuator, and a transmitter of the command to the patient-movement-actuator. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. Some implementations include a processor that is electrically coupled to the extractor, the processor being operable receive a command and the processor being operable to generate at least one instruction from the command in response to a sufficient authority, a sufficient level of emotional state, a sufficient competency and a sufficient state-of-mind of the command. Some implementations include a lift-device-controller that is electrically coupled to the patient-movement-actuator and that is operable to receive the at least one instruction and that is operable to generate at least one electrical signal from the at least one instruction, and a patient-movement-actuator that is operable to receive the at least one electrical signal. In some implementations, the multisensory input includes multisensory digital audio input. Some implementations include a computer-accessible medium that includes the receiver, and the extractor. In some implementations, the computer-accessible medium includes a field-programmable gate array. In some implementations, the field-programmable gate array is operable to filter environment background noise from the multisensory input. In some implementations, the field-programmable gate array is operable to extract from the multisensory input an indicator of an authority of the multisensory input, and identify an authority associated with the multisensory input from the indicator of the authority. In some implementations, identify the authority includes compare a speech pattern of a human speaker to a database of known humans, and determine an identity of the human speaker, yielding the authority of the identified human. In some implementations, the field-programmable gate array is operable to determine indicators of authority, emotional state, competency and state-of-mind in the multisensory input. In some implementations, the field-programmable gate array is operable to analyze the indicators of the authority, emotional state, competency and state-of-mind associated for sufficient levels of authority, emotional state, competency and state-of-mind that is required by the command. In some implementations, the transmitter includes a transmitter of the command to the patient-movement-actuator in response to sufficient levels of authority, emotional state, competency and state-of-mind that is required by the command.

In some aspects, an apparatus includes a field-programmable gate array that is operable to receive digital audio input, and extract a command relevant to a patient-movement-actuator, and a transmitter that is operable to send the command to a patient-movement-actuator-controller. Some implementations include a processor that is electrically coupled to the field-programmable gate array, the processor being operable receive the command and the processor being operable to generate at least one instruction from the command in response to a sufficient authority, a sufficient level of emotional state, a sufficient competency and a sufficient state-of-mind of the command, wherein the command sent to the patient-movement-actuator includes the at least one instruction. Some implementations include a lift-device-controller that is operable to receive the at least one instruction and that is operable to generate the at least one electrical signal from the at least one instruction, and a patient-movement-actuator that is electrically coupled to the lift-device-controller and that is operable to receive at least one electrical signal. In some implementations, the digital audio input includes multisensory digital audio input. In some implementations, the field-programmable gate array is operable to filter environment background noise from the digital audio input. In some implementations, the field-programmable gate array is operable to extract from the digital audio input an indicator of an authority of the digital audio input, identify an authority associated with the digital audio input from the indicator of the authority. In some implementations, identify the authority includes compare a speech pattern of a human speaker to a database of known humans, and determine an identity of the human speaker, yielding the authority of the identified human. In some implementations, the field-programmable gate array is operable to determine indicators of authority, emotional state, competency and state-of-mind in the digital audio input. In some implementations, the field-programmable gate array is operable to analyze the indicators of the authority, emotional state, competency and state-of-mind associated for sufficient levels of authority, emotional state, competency and state-of-mind that is required by the command In some implementations, the transmitter includes a transmitter of the command to the patient-movement-actuator in response to sufficient levels of authority, emotional state, competency and state-of-mind of the digital audio input is required by the command.

In some aspects, a method includes receiving multisensory digital audio input from a plurality of input devices, responsive to the receiving of the multisensory digital audio input, filtering environment background noise from the multisensory digital audio input, responsive to the filtering, extracting a command relevant to a patient-movement-actuator from the filtered multisensory digital audio input, responsive to the extracting of the command, extracting an indicator of an authority of the multisensory digital audio input from the filtered multisensory digital audio input, responsive to the extracting of the indicator of authority, identifying an authority associated with the multisensory digital audio input from the indicator of the authority, responsive to the identifying an authority, determining indicators of the emotional state, competency and state-of-mind in the multisensory digital audio input, responsive to the determining of the indicators, analyzing the indicators of the emotional state, competency and state-of-mind associated with the multisensory digital audio input for a sufficient level of emotional state, competency and state-of-mind that is required by the command, responsive to the analyzing of the indicators, generating at least one instruction from the command in response to a sufficient authority, a sufficient level of emotional state, a sufficient competency and a sufficient state-of-mind of the command, responsive to the generating of the at least one instruction, generating the at least one electrical signal from the at least one instruction by a lift-device-controller, and responsive to the generating the at least one electrical signal, transmitting the at least one electrical signal to a patient-movement-actuator. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, identifying the authority includes comparing a speech pattern of a human speaker to a database of known humans, and responsive to the comparing, determining an identity of the human speaker, yielding the authority of the identified human.

In some aspects, a method includes receiving multisensory digital audio input from the plurality of input devices, responsive to the receiving of the multisensory digital audio input, filtering environment background noise from the multisensory digital audio input, responsive to the filtering, extracting the command relevant to a patient-movement-actuator from the filtered multisensory digital audio input, responsive to the extracting of the command, extracting an indicator of an authority of the multisensory digital audio input from the filtered multisensory digital audio input, responsive to the extracting of the indicator of authority, identifying an authority associated with the multisensory digital audio input from the indicator of the authority, responsive to the identifying an authority, determining indicators of the emotional state, competency and state-of-mind in the multisensory digital audio input, and responsive to the determining of the indicators, analyzing the indicators of the emotional state, competency and state-of-mind associated with the multisensory digital audio input for a sufficient level of emotional state, competency and state-of-mind that is required by the command. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, identifying the authority includes comparing a speech pattern of a human speaker to a database of known humans, and responsive to the comparing, determining an identity of the human speaker, yielding the authority of the identified human. In some implementations, the method includes generating at least one instruction from the command in response to a sufficient authority, a sufficient level of emotional state, a sufficient competency and a sufficient state-of-mind of the command, responsive to the generating of the at least one instruction, generating the at least one electrical signal from the at least one instruction by a lift-device-controller, and responsive to the generating the at least one electrical signal, transmitting the at least one electrical signal from a patient-movement-actuator.

In some aspects, a method includes receiving multisensory input from a plurality of input devices, responsive to the receiving of the multisensory input, filtering environment background noise from the multisensory input, responsive to the filtering, extracting a command relevant to a patient-movement-actuator from the filtered multisensory input, responsive to the extracting of the command, extracting an indicator of an authority of the multisensory input from the filtered multisensory input, responsive to the extracting of the indicator of authority, identifying an authority associated with the multisensory input from the indicator of the authority, responsive to the identifying the authority, determining indicators of the emotional state, competency and state-of-mind in the multisensory input, responsive to the determining of the indicators, analyzing the indicators of the emotional state, competency and state-of-mind associated with the multisensory input for a sufficient level of emotional state, competency and state-of-mind that is required by the command. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, identify the authority includes comparing a speech pattern of a human speaker to a database of known humans, and responsive to the comparing, determining an identity of the human speaker, yielding the authority of the identified human. In some implementations, the method includes generating at least one instruction from the command in response to a sufficient authority, a sufficient level of emotional state, a sufficient competency and a sufficient state-of-mind of the command. In some implementations, the method includes generating at least one electrical signal from the at least one instruction by a lift-device-controller, and responsive to the generating the at least one electrical signal, transmitting the at least one electrical signal to a patient-movement-actuator. In some implementations, the multisensory input includes multisensory digital audio input.

In some aspects, a method includes receiving multisensory input from a plurality of input devices, responsive to the receiving of the multisensory input, extracting a command relevant to a patient-movement-actuator from the multisensory input, responsive to the extracting the command, extracting an indicator of an authority of the multisensory input from the multisensory input, responsive to the extracting of the indicator of the authority, identifying an authority associated with the multisensory input from the indicator of the authority, responsive to the identifying the authority, determining indicators of the emotional state, competency and state-of-mind in the multisensory input, responsive to the determining indicators, analyzing the indicators of the emotional state, competency and state-of-mind associated with the multisensory input for a sufficient level of emotional state, competency and state-of-mind that is required by the command. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, identify the authority includes comparing a speech pattern of a human speaker to a database of known humans, and responsive to the comparing, determining an identity of the human speaker, yielding the authority of the identified human. In some implementations, the method includes generating at least one instruction from the command in response to a sufficient authority, a sufficient level of emotional state, a sufficient competency and a sufficient state-of-mind of the command. In some implementations, the method includes generating at least one electrical signal from the at least one instruction by a lift-device-controller, and responsive to the generating of the at least one electrical signal, transmitting the at least one electrical signal to a patient-movement-actuator. In some implementations, the multisensory input includes multisensory digital audio input. In some implementations, the method includes responsive to the receiving of the multisensory input, filtering environment background noise from the multisensory input.

In some aspects, a method includes receiving multisensory input from a plurality of input devices, responsive to the receiving of the multisensory input, extracting a command relevant to a patient-movement-actuator from the multisensory input, responsive to the extracting of the command, determining indicators of authority, emotional state, competency and state-of-mind in the multisensory input, and responsive to the determining of the indicators of the authority, analyzing the indicators of the authority, emotional state, competency and state-of-mind associated with the multisensory input for a sufficient level of emotional state, competency and state-of-mind that is required by the command. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, the method includes identifying an authority associated with the multisensory digital audio input from the indicator of the authority. In some implementations, identifying the authority includes comparing a speech pattern of a human speaker to a database of known humans, and responsive to comparing, determining an identity of the human speaker, yielding the authority of the identified human. In some implementations, the method includes generating at least one instruction from the command in response to a sufficient authority, a sufficient level of emotional state, a sufficient competency and a sufficient state-of-mind of the command. In some implementations, the method includes generating at least one electrical signal from the at least one instruction by a lift-device-controller, and responsive to the generating of the at least one electrical signal, transmitting the at least one electrical signal to a patient-movement-actuator. In some implementations, the multisensory input includes multisensory digital audio input. In some implementations, the method includes responsive to the receiving of the multisensory digital audio input, filtering environment background noise from the multisensory input.

In some aspects, a method includes receiving multisensory input from a plurality of input devices, responsive to the receiving of the multisensory input, extracting a command relevant to a patient-movement-actuator from the multisensory input, responsive to the extracting a command, determining an indicator of authority, emotional state, competency and state-of-mind in the multisensory input, responsive to the determining of the indicator of the authority, analyzing the indicators of the authority, emotional state, competency and state-of-mind associated with the multisensory input for a sufficient level of emotional state, competency and state-of-mind that is required by the command, and responsive to sufficient levels of authority, emotional state, competency and state-of-mind that is required by the command, transmitting the command to the patient-movement-actuator. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, the method includes identifying an authority associated with the multisensory digital audio input from the indicator of the authority. In some implementations, identifying the authority includes comparing a speech pattern of a human speaker to a database of known humans, and responsive to the comparing, determining an identity of the human speaker, yielding the authority of the identified human. In some implementations, the method includes generating at least one instruction from the command in response to a sufficient authority, a sufficient level of emotional state, a sufficient competency and a sufficient state-of-mind of the command. In some implementations, the method includes generating at least one electrical signal from the at least one instruction by a lift-device-controller, and responsive to the generating of the at least one electrical signal, transmitting the at least one electrical signal to a patient-movement-actuator. In some implementations, the multisensory input includes multisensory digital audio input. In some implementations, the method includes responsive to the receiving of the multisensory input, filtering environment background noise from the multisensory input. In some implementations, the method includes extracting from the multisensory input an indicator of an authority of the multisensory input, and identifying the authority associated with the multisensory input from the indicator of the authority.

In some aspects, a method includes receiving multisensory input from a plurality of input devices, responsive to the receiving of the multisensory input, extracting a command relevant to a patient-movement-actuator from the multisensory input, responsive to the extracting of the command, analyzing indicators of the authority, emotional state, competency and state-of-mind associated with the multisensory input for a sufficient level of emotional state, competency and state-of-mind that is required by the command, and responsive to sufficient levels of authority, emotional state, competency and state-of-mind that is required by the command, transmitting the command to the patient-movement-actuator. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, the method includes identifying an authority associated with the multisensory digital audio input from the indicator of the authority. In some implementations, identifying the authority includes comparing a speech pattern of a human speaker to a database of known humans, and responsive to the comparing, determining an identity of the human speaker, yielding the authority of the identified human. In some implementations, the method includes extracting from the multisensory input an indicator of the authority of the multisensory input, and responsive to the extracting the indicator of the authority, identifying the authority associated with the multisensory input from the indicator of the authority. In some implementations, the method includes determining the indicators of authority, emotional state, competency and state-of-mind in the multisensory input. In some implementations, the method includes generating at least one instruction from the command in response to a sufficient authority, a sufficient level of emotional state, a sufficient competency and a sufficient state-of-mind of the command. In some implementations, the method includes generating at least one electrical signal from the at least one instruction by a lift-device-controller, and responsive to the generating of the at least one electrical signal, transmitting the at least one electrical signal to a patient-movement-actuator. In some implementations, the multisensory input includes multisensory digital audio input. In some implementations, the method includes responsive to the receiving of the multisensory input, filtering environment background noise from the multisensory input.

In some aspects, a method includes receiving multisensory input from a plurality of input devices, responsive to the receiving of the multisensory digital audio input, extracting a command relevant to a patient-movement-actuator from the multisensory input, and responsive to the extracting of the command, will transmitting the command to the patient-movement-actuator. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, the method includes identifying an authority associated with the multisensory digital audio input from the indicator of the authority. In some implementations, identifying the authority includes comparing a speech pattern of a human speaker to a database of known humans, and responsive to the comparing, or determining an identity of the human speaker, yielding the authority of the identified human. In some implementations, the method includes generating at least one instruction from the command in response to a sufficient authority, a sufficient level of emotional state, a sufficient competency and a sufficient state-of-mind of the command. In some implementations, the method includes generating at least one electrical signal from the at least one instruction by a lift-device-controller, and responsive to the generating of the at least one electrical signal, transmitting the at least one electrical signal to the patient-movement-actuator. In some implementations, the multisensory input includes multisensory digital audio input. In some implementations, the method includes responsive to the receiving of the multisensory input, filtering environment background noise from the multisensory input. In some implementations, the method includes extracting from the multisensory input an indicator of an authority of the multisensory input, and responsive to the extracting of the indicator of the authority, identifying an authority associated with the multisensory input from the indicator of the authority. In some implementations, the method includes determining the indicators of authority, emotional state, competency and state-of-mind in the multisensory input.

In some aspects, a method includes extracting a patient-lifting-device command from multisensory input, and responsive to the extracting of the patient-lifting-device command, will transmitting the command to the patient-movement-actuator. In some implementations, identify the authority includes comparing a speech pattern of a human speaker to a database of known humans, and in the comparing, determining an identity of the human speaker, yielding the authority of the identified human. In some implementations, the method includes response to the extracting of the patient-lifting-device command, generating at least one instruction from the command in response to a sufficient authority, a sufficient level of emotional state, a sufficient competency and a sufficient state-of-mind of the command. In some implementations, the method includes responsive to the generating of the at least one instruction, generating at least one electrical signal from the at least one instruction by a lift-device-controller, and responsive to the generating of the at least one electrical signal, transmitting the at least one electrical signal to a patient-movement-actuator. In some implementations, the multisensory input includes multisensory digital audio input. In some implementations, the method includes responsive to the receiving of the multisensory digital audio input, filtering environment background noise from the multisensory digital audio input. In some implementations, the method includes responsive to the receiving of the multisensory input, filtering environment background noise from the multisensory input. In some implementations, the method includes extracting from the multisensory input an indicator of an authority of the multisensory input, and identifying an authority associated with the multisensory input from the indicator of the authority. In some implementations, the method includes determining the indicators of authority, emotional state, competency and state-of-mind in the multisensory input. In some implementations, the method includes receiving the multisensory input from a plurality of input devices. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection.

In some aspects, a computer-accessible medium has computer executable instructions to control a patient-movement-actuator, the computer executable instructions capable of directing a processor to perform receiving multisensory digital audio input from a plurality of input devices, filtering environment background noise from the multisensory digital audio input, extracting a command relevant to the patient-movement-actuator from the filtered multisensory digital audio input, extracting an indicator of an authority of the multisensory digital audio input from the filtered multisensory digital audio input, identifying an authority associated with the multisensory digital audio input will from the indicator of the authority, determining indicators of the emotional state, competency and state-of-mind in the multisensory digital audio input, analyzing the indicators of the emotional state, competency and state-of-mind associated with the multisensory digital audio input for a sufficient level of emotional state, competency and state-of-mind that is required by the command, generating at least one instruction from the command in response to a sufficient authority, a sufficient level of emotional state, a sufficient competency and a sufficient state-of-mind of the command, generating the at least one electrical signal from the at least one instruction by a lift-device-controller, and transmitting the at least one electrical signal to the patient-movement-actuator. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, the computer accessible medium includes the computer executable instructions capable of directing the processor to identify the authority includes computer executable instructions capable of directing the processor to perform comparing a speech pattern of a human speaker to a database of known humans, and determining an identity of the human speaker, yielding the authority of the identified human.

In some aspects, a computer-accessible medium has computer executable instructions to control a patient-movement-actuator, the computer executable instructions capable of directing a processor to perform receiving multisensory digital audio input from the plurality of input devices, filtering environment background noise from the multisensory digital audio input, extracting the command relevant to the patient-movement-actuator from the filtered multisensory digital audio input, extracting an indicator of an authority of the multisensory digital audio input from the filtered multisensory digital audio input, identifying an authority associated with the multisensory digital audio input from the indicator of the authority, determining indicators of the emotional state, competency and state-of-mind in the multisensory digital audio input, and analyzing the indicators of the emotional state, competency and state-of-mind associated with the multisensory digital audio input for a sufficient level of emotional state, competency and state-of-mind that is required by the command. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, the computer accessible medium includes the computer executable instructions capable of directing the processor to identify the authority includes computer executable instructions capable of directing the processor to perform comparing a speech pattern of a human speaker to a database of known humans, and determining an identity of the human speaker, yielding the authority of the identified human. In some implementations, the computer accessible medium includes computer executable instructions capable of directing the processor to perform generating at least one instruction from the command in response to a sufficient authority, a sufficient level of emotional state, a sufficient competency and a sufficient state-of-mind of the command, generating the at least one electrical signal from the at least one instruction by a lift-device-controller, and transmitting the at least one electrical signal to the patient-movement-actuator.

In some aspects, a computer-accessible medium has computer executable instructions to control a patient-movement-actuator, the computer executable instructions capable of directing a processor to perform receiving multisensory input from a plurality of input devices, filtering environment background noise from the multisensory input, responsive to the filtering, extracting a command relevant to the patient-movement-actuator from the filtered multisensory input, extracting an indicator of an authority of the multisensory input from the filtered multisensory input, identifying an authority associated with the multisensory input from the indicator of the authority, determining indicators of the emotional state, competency and state-of-mind in the multisensory input, analyzing the indicators of the emotional state, competency and state-of-mind associated with the multisensory input for a sufficient level of emotional state, competency and state-of-mind that is required by the command. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, the computer accessible medium includes identify the authority includes comparing a speech pattern of a human speaker to a database of known humans, and determining an identity of the human speaker, yielding the authority of the identified human. In some implementations, the computer accessible medium includes computer executable instructions capable of directing the processor to perform generating at least one instruction from the command in response to a sufficient authority, a sufficient level of emotional state, a sufficient competency and a sufficient state-of-mind of the command. In some implementations, the computer accessible medium includes computer executable instructions capable of directing the processor to perform generating at least one electrical signal from the at least one instruction by a lift-device-controller, and transmitting the at least one electrical signal to the patient-movement-actuator. In some implementations, the computer accessible medium includes the multisensory input includes multisensory digital audio input.

In some aspects, a computer-accessible medium has computer executable instructions to control a patient-movement-actuator, the computer executable instructions capable of directing a processor to perform receiving multisensory input from a plurality of input devices, extracting a command relevant to the patient-movement-actuator from the multisensory input, extracting an indicator of an authority of the multisensory input from the multisensory input, identifying an authority associated with the multisensory input from the indicator of the authority, determining indicators of the emotional state, competency and state-of-mind in the multisensory input, analyzing the indicators of the emotional state, competency and state-of-mind associated with the multisensory input for a sufficient level of emotional state, competency and state-of-mind that is required by the command. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, the computer accessible medium includes identify the authority includes comparing a speech pattern of a human speaker to a database of known humans, and determining an identity of the human speaker, yielding the authority of the identified human. In some implementations, the computer accessible medium includes computer executable instructions capable of directing the processor to perform generating at least one instruction from the command in response to a sufficient authority, a sufficient level of emotional state, a sufficient competency and a sufficient state-of-mind of the command. In some implementations, the computer accessible medium includes computer executable instructions capable of directing the processor to perform generating at least one electrical signal from the at least one instruction by a lift-device-controller, and transmitting the at least one electrical signal to the patient-movement-actuator. In some implementations, the computer accessible medium includes the multisensory input includes multisensory digital audio input. In some implementations, the computer accessible medium includes filtering environment background noise from the multisensory input.

In some aspects, a computer-accessible medium has computer executable instructions to control a patient-movement-actuator, the computer executable instructions capable of directing a processor to perform receiving multisensory input from a plurality of input devices, extracting a command relevant to the patient-movement-actuator from the multisensory input, determining indicators of authority, emotional state, competency and state-of-mind in the multisensory input, and analyzing the indicators of the authority, emotional state, competency and state-of-mind associated with the multisensory input for a sufficient level of emotional state, competency and state-of-mind that is required by the command. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, the computer accessible medium includes computer executable instructions capable of directing the processor to perform identifying an authority associated with the multisensory digital audio input from the indicator of the authority. In some implementations, the computer accessible medium includes the computer executable instructions capable of directing the processor to identify the authority includes computer executable instructions capable of directing the processor to perform comparing a speech pattern of a human speaker to a database of known humans, and determining an identity of the human speaker, yielding the authority of the identified human. In some implementations, the computer accessible medium includes computer executable instructions capable of directing the processor to perform generating at least one instruction from the command in response to a sufficient authority, a sufficient level of emotional state, a sufficient competency and a sufficient state-of-mind of the command. In some implementations, the computer accessible medium includes computer executable instructions capable of directing the processor to perform generating at least one electrical signal from the at least one instruction by a lift-device-controller, and transmitting the at least one electrical signal to the patient-movement-actuator. In some implementations, the computer accessible medium includes the multisensory input includes multisensory digital audio input. In some implementations, the computer accessible medium includes computer executable instructions capable of directing the processor to perform filtering environment background noise from the multisensory input.

In some aspects, a computer-accessible medium has computer executable instructions to control a patient-movement-actuator, the computer executable instructions capable of directing a processor to perform receiving multisensory input from a plurality of input devices, extracting a command relevant to the patient-movement-actuator from the multisensory input, determining indicators of authority, emotional state, competency and state-of-mind in the multisensory input, analyzing the indicators of the authority, emotional state, competency and state-of-mind associated with the multisensory input for a sufficient level of emotional state, competency and state-of-mind that is required by the command, and responsive to sufficient levels of authority, emotional state, competency and state-of-mind that is required by the command, transmitting the command to the patient-movement-actuator. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, the computer accessible medium includes computer executable instructions capable of directing the processor to perform identifying an authority associated with the multisensory digital audio input from the indicator of the authority. In some implementations, the computer accessible medium includes the computer executable instructions capable of directing the processor to identify the authority includes computer executable instructions capable of directing the processor to perform comparing a speech pattern of a human speaker to a database of known humans, and determining an identity of the human speaker, yielding the authority of the identified human. In some implementations, the computer accessible medium includes computer executable instructions capable of directing the processor to perform generating at least one instruction from the command in response to a sufficient authority, a sufficient level of emotional state, a sufficient competency and a sufficient state-of-mind of the command. In some implementations, the computer accessible medium includes computer executable instructions capable of directing the processor to perform generating at least one electrical signal from the at least one instruction by a lift-device-controller, and transmitting the at least one electrical signal to the patient-movement-actuator. In some implementations, the computer accessible medium includes the multisensory input includes multisensory digital audio input. In some implementations, the computer accessible medium includes computer executable instructions capable of directing the processor to perform filtering environment background noise from the multisensory input. In some implementations, the computer accessible medium includes computer executable instructions capable of directing the processor to perform extracting from the multisensory input an indicator of an authority of the multisensory input, and identifying the authority associated with the multisensory input from the indicator of the authority.

In some aspects, a computer-accessible medium has computer executable instructions to control a patient-movement-actuator, the computer executable instructions capable of directing a processor to perform receiving multisensory input from a plurality of input devices, extracting a command relevant to the patient-movement-actuator from the multisensory input, analyzing indicators of the authority, emotional state, competency and state-of-mind associated with the multisensory input for a sufficient level of emotional state, competency and state-of-mind that is required by the command, and responsive to sufficient levels of authority, emotional state, competency and state-of-mind that is required by the command, transmitting the command to the patient-movement-actuator. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, the computer accessible medium includes computer executable instructions capable of directing the processor to perform identifying an authority associated with the multisensory digital audio input from the indicator of the authority. In some implementations, the computer accessible medium includes the computer executable instructions capable of directing the processor to identify the authority includes computer executable instructions capable of directing the processor to perform comparing a speech pattern of a human speaker to a database of known humans, and determining an identity of the human speaker, yielding the authority of the identified human. In some implementations, the computer accessible medium includes computer executable instructions capable of directing the processor to perform extracting from the multisensory input an indicator of the authority of the multisensory input, and identifying the authority associated with the multisensory input from the indicator of the authority. In some implementations, the computer accessible medium includes computer executable instructions capable of directing the processor to perform determining the indicators of authority, emotional state, competency and state-of-mind in the multisensory input. In some implementations, the computer accessible medium includes computer executable instructions capable of directing the processor to perform generating at least one instruction from the command in response to a sufficient authority, a sufficient level of emotional state, a sufficient competency and a sufficient state-of-mind of the command. In some implementations, the computer accessible medium includes computer executable instructions capable of directing the processor to perform generating at least one electrical signal from the at least one instruction by a lift-device-controller, and transmitting the at least one electrical signal to the patient-movement-actuator. In some implementations, the computer accessible medium includes the multisensory input includes multisensory digital audio input. In some implementations, the computer accessible medium includes computer executable instructions capable of directing the processor to perform filtering environment background noise from the multisensory input.

In some aspects, a computer-accessible medium has computer executable instructions to control a patient-movement-actuator, the computer executable instructions capable of directing a processor to perform receiving multisensory input from a plurality of input devices, extracting a command relevant to the patient-movement-actuator from the multisensory input, and transmitting the command to the patient-movement-actuator. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection. In some implementations, the computer accessible medium includes computer executable instructions capable of directing the processor to perform identifying an authority associated with the multisensory digital audio input from the indicator of the authority. In some implementations, the computer accessible medium includes the computer executable instructions capable of directing the processor to identify the authority includes computer executable instructions capable of directing the processor to perform comparing a speech pattern of a human speaker to a database of known humans, and determining an identity of the human speaker, yielding the authority of the identified human. In some implementations, the computer accessible medium includes computer executable instructions capable of directing the processor to perform generating at least one instruction from the command in response to a sufficient authority, a sufficient level of emotional state, a sufficient competency and a sufficient state-of-mind of the command. In some implementations, the computer accessible medium includes computer executable instructions capable of directing the processor to perform generating at least one electrical signal from the at least one instruction by a lift-device-controller, and transmitting the at least one electrical signal to the patient-movement-actuator. In some implementations, the computer accessible medium includes the multisensory input includes multisensory digital audio input. In some implementations, the computer accessible medium includes computer executable instructions capable of directing the processor to perform filtering environment background noise from the multisensory input. In some implementations, the computer accessible medium includes computer executable instructions capable of directing the processor to perform extracting from the multisensory input an indicator of an authority of the multisensory input, and identifying an authority associated with the multisensory input from the indicator of the authority. In some implementations, the computer accessible medium includes computer executable instructions capable of directing the processor to perform determining the indicators of authority, emotional state, competency and state-of-mind in the multisensory input.

In some aspects, a computer-accessible medium has computer executable instructions to control a patient-movement-actuator, the computer executable instructions capable of directing a processor to perform extracting a patient-lifting-device command from multisensory input, and transmitting the command to the patient-movement-actuator. In some implementations, the computer accessible medium includes identify the authority includes comparing a speech pattern of a human speaker to a database of known humans, and determining an identity of the human speaker, yielding the authority of the identified human. In some implementations, the computer accessible medium includes computer executable instructions capable of directing the processor to perform generating at least one instruction from the command in response to a sufficient authority, a sufficient level of emotional state, a sufficient competency and a sufficient state-of-mind of the command. In some implementations, the computer accessible medium includes computer executable instructions capable of directing the processor to perform generating at least one electrical signal from the at least one instruction by a lift-device-controller, and transmitting the at least one electrical signal to the patient-movement-actuator. In some implementations, the computer accessible medium includes the multisensory input includes multisensory digital audio input. In some implementations, the computer accessible medium includes computer executable instructions capable of directing the processor to perform filtering environment background noise from the multisensory audio digital input. In some implementations, the computer accessible medium includes computer executable instructions capable of directing the processor to perform filtering environment background noise from the multisensory input. In some implementations, the computer accessible medium includes computer executable instructions capable of directing the processor to perform extracting from the multisensory input an indicator of an authority of the multisensory input, and identifying an authority associated with the multisensory input from the indicator of the authority. In some implementations, the computer accessible medium includes computer executable instructions capable of directing the processor to perform determining the indicators of authority, emotional state, competency and state-of-mind in the multisensory input. In some implementations, the computer accessible medium includes computer executable instructions capable of directing the processor to perform receiving the multisensory input from a plurality of input devices, In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection. In some implementations, the plurality of input devices includes a wired connection.

In some aspects a patient-movement-actuator includes a plurality of input devices, a receiver of multisensory digital audio input from the plurality of input devices, the receiver of multisensory digital audio input being operably coupled to the plurality of input devices, a filter of the environment background noise from the multisensory digital audio input, the filter of environment background noise being operably coupled to the receiver of the multisensory digital audio input, a command-extractor that is operable to extract from the filtered multisensory digital audio input a command that is relevant to a patient-movement-actuator, the command-extractor being operably coupled to the filter, an authority-detector that is operable to extract an indicator of an authority from the multisensory digital audio input, the authority-detector being operably coupled to the filter, an authority-identifier that is operable to identify an authority associated with the multisensory digital audio input from the indicator of the authority, the authority-identifier being operably coupled to the authority-detector, a subjective-analyzer that is operable to determine indicators of an emotional state, a competency and a state-of-mind in the multisensory digital audio input, the subjective-analyzer operably coupled to the filter, a final-analyzer that is operable to determine whether or not the indicator of the authority, the indicator of the emotional state, the indicator of the competency and the indicator of the state-of-mind all have a sufficient level of authority emotional state, competency and state-of-mind that is required by the command, the final analyzer being operably coupled to the authority-indicator and the subjective-analyzer, an instruction-generator that is operable to receive the command and that is operable to generate at least one instruction from the command in response to a sufficient authority, a sufficient level of emotional state, a sufficient competency and a sufficient state-of-mind of the command, the instruction-generator being electrically coupled to the final-analyzer, and a lift-device-controller that is operable to receive at least one instruction from the instruction-generator and that is operable to generate at least one electrical signal from the at least one instruction, the lift-device-controller being electrically coupled to the instruction-generator, and a patient-movement-actuator that is operable to receive at least one electrical signal and operable to perform motion in accordance with the at least one electrical signal and in response to the at least one electrical signal. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection to the receiver. In some implementations, the plurality of input devices includes a wired connection to the receiver. In some implementations, identifying the authority includes comparing a speech pattern of a human speaker to a database of known humans, and determining an identity of the human speaker, yielding the authority of the identified human.

In some aspects a patient-movement-actuator includes a plurality of input devices, a receiver of multisensory digital audio input from the plurality of input devices, the receiver of multisensory digital audio input being operably coupled to the plurality of input devices, a filter of the environment background noise from the multisensory digital audio input, the filter of environment background noise being operably coupled to the receiver of the multisensory digital audio input, a command-extractor that is operable to extract from the filtered multisensory digital audio input a command that is relevant to a patient-movement-actuator, the command-extractor being operably coupled to the filter, a lift-device-controller that is operable to receive the command from the command-extractor and that is operable to generate at least one electrical signal from the command, the lift-device-controller being electrically coupled to the command-extractor, and a patient-movement-actuator that is operable to receive at least one electrical signal and operable to perform motion in accordance with the at least one electrical signal and in response to the at least one electrical signal. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection to the receiver. In some implementations, the plurality of input devices includes a wired connection to the receiver. Some implementations include an authority-detector that is operable to extract an indicator of an authority from the multisensory digital audio input, the authority-detector being operably coupled to the filter, an authority-identifier that is operable to identify an authority associated with the multisensory digital audio input from the indicator of the authority, the authority-identifier being operably coupled to the authority-detector, a subjective-analyzer that is operable to determine indicators of an emotional state, a competency and a state-of-mind in the multisensory digital audio input, the subjective-analyzer operably coupled to the filter, a final-analyzer that is operable to determine whether or not the indicator of the authority, the indicator of the emotional state, the indicator of the competency and the indicator of the state-of-mind all have a sufficient level of authority emotional state, competency and state-of-mind that is required by the command, the final analyzer being operably coupled to the authority-indicator and the subjective-analyzer. In some implementations, the instruction-generator includes an instruction-generator that is operable to receive the command and that is operable to generate at least one instruction from the command in response to a sufficient authority, a sufficient level of emotional state, a sufficient competency and a sufficient state-of-mind of the command, the instruction-generator being electrically coupled to the final-analyzer. In some implementations, identifying the authority includes comparing a speech pattern of a human speaker to a database of known humans, and determining an identity of the human speaker, yielding the authority of the identified human.

In some aspects, a patient-movement-actuator includes a receiver of multisensory digital audio input from a plurality of input devices, the receiver of multisensory digital audio input, a command-extractor that is operable to extract from the multisensory digital audio input a command that is relevant to a patient-movement-actuator, the command-extractor being operably coupled to the filter, a lift-device-controller that is operable to receive the command from the command-extractor and that is operable to generate at least one electrical signal from the command, the lift-device-controller being electrically coupled to the command-extractor, and a patient-movement-actuator that is operable to receive at least one electrical signal and operable to perform motion in accordance with the at least one electrical signal and in response to the at least one electrical signal. Some implementations include a filter of the environment background noise from the multisensory digital audio input, the filter of environment background noise being operably coupled to the receiver of the multisensory digital audio input and operably coupled to the command-extractor. In some implementations, the plurality of input devices includes a keypad controller, and a microphone. In some implementations, the plurality of input devices is selected from the group of input devices consisting of a keypad controller and a microphone. In some implementations, the plurality of input devices is selected from the group of input devices consisting essentially of a keypad controller and a microphone. In some implementations, the plurality of input devices includes a keyboard, a microphone, and a synaptic activity sensor. In some implementations, the plurality of input devices is selected from the group of input devices consisting of a keyboard, a microphone, and a synaptic activity sensor. In some implementations, the plurality of input devices includes a wireless connection to the receiver. In some implementations, the plurality of input devices includes a wired connection to the receiver. Some implementations include an authority-detector that is operable to extract an indicator of an authority from the multisensory digital audio input, the authority-detector being operably coupled to the filter, an authority-identifier that is operable to identify an authority associated with the multisensory digital audio input from the indicator of the authority, the authority-identifier being operably coupled to the authority-detector, a subjective-analyzer that is operable to determine indicators of an emotional state, a competency and a state-of-mind in the multisensory digital audio input, the subjective-analyzer operably coupled to the filter, a final-analyzer that is operable to determine whether or not the indicator of the authority, the indicator of the emotional state, the indicator of the competency and the indicator of the state-of-mind all have a sufficient level of authority emotional state, competency and state-of-mind that is required by the command, the final analyzer being operably coupled to the authority-indicator and the subjective-analyzer. Some implementations include an instruction-generator that is operable to receive the command and that is operable to generate at least one instruction from the command in response to a sufficient authority, a sufficient level of emotional state, a sufficient competency and a sufficient state-of-mind of the command, the instruction-generator being electrically coupled to the final-analyzer. In some implementations, identifying the authority includes comparing a speech pattern of a human speaker to a database of known humans, and determine an identity of the human speaker, yielding the authority of the identified human.

In some aspects a patient-movement-actuator includes a plurality of input devices, the plurality of devices consisting of a hand-held keypad controller and a microphone, a receiver of multisensory digital audio input from the plurality of input devices, the receiver of multisensory digital audio input being operably coupled to the plurality of input devices, a filter of the environment background noise from the multisensory digital audio input, the filter of environment background noise being operably coupled to the receiver of the multisensory digital audio input, a command-extractor that is operable to extract from the filtered multisensory digital audio input a patient-lifting-device command, the command-extractor being operably coupled to the filter, a lift-device-controller that is operable to receive the patient-lifting-device command from the command-extractor and that is operable to generate at least one electrical signal from the patient-lifting-device command, the lift-device-controller being electrically coupled to the command-extractor, and a patient-movement-actuator that is operable to receive at least one electrical signal and operable to perform motion in accordance with the at least one electrical signal and in response to the at least one electrical signal. In some implementations, the plurality of input devices consists of a microphone. In some implementations, the plurality of input devices includes a wireless connection to the receiver. In some implementations, the plurality of input devices includes a wired connection to the receiver. Some implementations include an authority-detector that is operable to extract an indicator of an authority from the multisensory digital audio input, the authority-detector being operably coupled to the filter, an authority-identifier that is operable to identify an authority associated with the multisensory digital audio input from the indicator of the authority, the authority-identifier being operably coupled to the authority-detector, a subjective-analyzer that is operable to determine indicators of an emotional state, a competency and a state-of-mind in the multisensory digital audio input, the subjective-analyzer operably coupled to the filter, a final-analyzer that is operable to determine whether or not the indicator of the authority, the indicator of the emotional state, the indicator of the competency and the indicator of the state-of-mind all have a sufficient level of authority emotional state, competency and state-of-mind that is required by the patient-lifting-device command, the final analyzer being operably coupled to the authority-indicator and the subjective-analyzer. Some implementations include an instruction-generator that is operable to receive the patient-lifting-device command and that is operable to generate at least one instruction from the patient-lifting-device command in response to a sufficient authority, from which the at least one electrical signal is generated, responsive to a sufficient level of emotional state, a sufficient competency and a sufficient state-of-mind of the patient-lifting-device command, the instruction-generator being electrically coupled to the final-analyzer. In some implementations, identifying the authority includes comparing a speech pattern of a human speaker to a database of known humans, and determine an identity of the human speaker, yielding the authority of the identified human.

In some aspects, a method includes receiving multisensory digital input from a plurality of input devices, the plurality of devices consisting of a hand-held keypad controller and a microphone, responsive to the receiving out multisensory digital input, filtering environment background noise from the multisensory digital input, responsive to the filtering environment background noise from the multisensory digital input, extracting a command from the filtered multisensory digital input, responsive to the extracting of a command from the filtered multisensory digital input, generating at least one electrical signal from the patient-lifting-device command, and responsive to the generating of the at least one the electrical signal, performing motion in accordance with the at least one electrical signal. In some implementations, the plurality of input devices consists of a microphone. In some implementations, the plurality of input devices includes a wireless connection to the receiver. In some implementations, the plurality of input devices includes a wired connection to the receiver. In some implementations, the method includes extracting an indicator of an authority from the multisensory digital input, identifying an authority associated with the multisensory digital input from the indicator of the authority, determining indicators of an emotional state, a competency and a state-of-mind in the multisensory digital input, the subjective-analyzer operably coupled to the filter, determining whether or not the indicator of the authority, the indicator of the emotional state, the indicator of the competency and the indicator of the state-of-mind have a sufficient level of authority emotional state, competency and state-of-mind that is required by the patient-lifting-device command. In some implementations, the method includes generating at least one instruction from the patient-lifting-device command from the command, responsive to a sufficient level of emotional state, a sufficient competency and a sufficient state-of-mind of the patient-lifting-device command. In some implementations, identifying the authority includes comparing a speech pattern of a human speaker to a database of known humans, and determining an identity of the human speaker, yielding the authority of the identified human.

In some aspects, a computer-accessible medium has executable instructions to control a patient-movement-actuator, the executable instructions capable of directing a processor to perform receiving audio information from a microphone, filtering environment background noise from the audio information, extracting a command associated with the patient-movement-actuator, and performing the command by a lift-device-controller of the patient-movement-actuator. In some implementations the medium includes executable instructions capable of directing a processor to perform extracting from the audio information an indicator of the authority of the speaker of the audio information. In some implementations, the computer accessible medium includes the extracting includes identifying the speaker of the audio information. In some implementations, the computer accessible medium includes the identifying includes comparing a speech pattern of the human speaker a database of known humans, and determining an identity of the human speaker, yielding the authority of the identified human.

In some aspects, a computer-accessible medium has executable instructions to update a database of authorities of a patient-lifting-device, the executable instructions capable of directing a processor to perform recording a speech sample of a human, the human selected from the group of humans comprising human healthcare providers, human non-professional employees of a healthcare facility, patients, and friends, relatives and coworkers of the patient, and associating the recording with an authority of control of the patient-movement-actuator. In some implementations, the computer accessible medium includes the authority is selected from the group of authorities comprising a full authority in which the human is authorized to exercise or command all functions of the patient-movement-actuator, and no authority in which the human is not authorized to exercise or command any function of the patient-lifting-device.

The invention claimed is:

1. An apparatus comprising:
a receiver of multisensory digital audio input from a plurality of input devices, the receiver of multisensory digital audio input;
a command-extractor that is operable to extract from the multisensory digital audio input a command that is relevant to a patient-movement-actuator, the command-extractor being operably coupled to the receiver;
a lift-device-controller that is operable to receive the command from the command-extractor and that is operable to generate at least one electrical signal from the command, the lift-device-controller being electrically coupled to the command-extractor; and a patient-movement-actuator that is operable to receive at least one electrical signal and operable to perform motion in accordance with the at least one electrical signal and in response to the at least one electrical signal.

2. The apparatus of claim 1 further comprising:
a filter of environment background noise from the multisensory digital audio input, the filter of environment background noise being operably coupled to the receiver of the multisensory digital audio input and operably coupled to the command-extractor.

3. The apparatus of claim 1 wherein the plurality of input devices further comprises:
a keypad controller; and
a microphone.

4. The apparatus of claim 1 wherein the plurality of input devices is selected from the group of input devices consisting of a keypad controller and a microphone.

5. The apparatus of claim 1 wherein the plurality of input devices is selected from the group of input devices consisting essentially of a keypad controller and a microphone.

6. The apparatus of claim 1 wherein the plurality of input devices further comprises:
a keyboard;
a microphone; and
a synaptic activity sensor.

7. The apparatus of claim 1 wherein the plurality of input devices is selected from the group of input devices consisting of a keyboard, a microphone, and a synaptic activity sensor.

8. The apparatus of claim 1 wherein the plurality of input devices further comprises:
a wireless connection to the receiver.

9. The apparatus of claim 1 wherein the plurality of input devices further comprises:
a wired connection to the receiver.

10. The apparatus of claim 1 wherein the patient-movement-actuator further comprises:
a normally-open double-pole-double-throw (DPDT) relay.

11. The apparatus of claim 1 wherein the command-extractor further comprises:
a voice recognition unit.

12. The apparatus of claim 1 further comprising:
an authority-detector that is operable to extract an indicator of an authority from the multisensory digital audio input; the authority-detector being operably coupled to the filter;
an authority-identifier that is operable to identify an authority associated with the multisensory digital audio input from the indicator of the authority; the authority-identifier being operably coupled to the authority-detector;
a subjective-analyzer that is operable to determine indicators of an emotional state, a competency and a state-of-mind in the multisensory digital audio input; the subjective-analyzer operably coupled to the filter;
a final-analyzer that is operable to determine whether or not the indicator of the authority, the indicator of the emotional state, the indicator of the competency and the indicator of the state-of-mind all have a sufficient level of authority emotional state, competency and state-of-mind that is required by the command, the final analyzer being operably coupled to the authority-indicator and the subjective-analyzer.

13. A method comprising:
receiving multisensory input from a plurality of input devices, the plurality of devices consisting of a handheld keypad controller and a microphone;
responsive to the receiving of multisensory input, filtering environment background noise from the multisensory input, yielding filtered multisensory input;
responsive to the filtering environment background noise from the multisensory input, extracting a patient-lifting-device command from the filtered multisensory input;
responsive to the extracting of the patient-lifting-device command from the filtered multisensory input, generating at least one electrical signal from the patient-lifting-device command; and
responsive to the generating of the at least one the electrical signal, performing motion of a patient-lifting-device in accordance with the at least one electrical signal.

14. The method of claim 13 wherein the plurality of input devices consists of:
the microphone.

15. The method of claim 13 wherein the plurality of input devices further comprises:
a wireless connection to the receiver.

16. The method of claim 13 wherein the plurality of input devices further comprises:
a wired connection to the receiver.

17. The method of claim 13 wherein extracting the patient-lifting-device command from the filtered multisensory input further comprises:
voice recognition on input from the microphone.

18. The method of claim 13 further comprising:
extracting an indicator of an authority from the multisensory input;
identifying an authority associated with the multisensory input from the indicator of the authority;
determining indicators of an emotional state, a competency and a state-of-mind in the multisensory input; the subjective-analyzer operably coupled to the filter; and
determining whether or not the indicator of the authority, the indicator of the emotional state, the indicator of the competency and the indicator of the state-of-mind have a sufficient level of authority emotional state, competency and state-of-mind that is required by the patient-lifting-device command.

19. The method of claim 18 further comprising:
generating at least one instruction from the patient-lifting-device command from the command, responsive to a sufficient level of emotional state, a sufficient competency and a sufficient state-of-mind of the patient-lifting-device command.

20. The method of claim 18 wherein identifying the authority further comprises:
comparing a speech pattern of a human speaker to a database of known humans; and
determining an identity of the human speaker, yielding the authority of the identified human.

* * * * *